(12) United States Patent
Jayaraman et al.

(10) Patent No.: US 10,071,092 B2
(45) Date of Patent: Sep. 11, 2018

(54) POLYMORPHIC FORMS OF VORTIOXETINE AND ITS PHARMACEUTICALLY ACCEPTABLE SALTS

(71) Applicant: ALEMBIC PHARMACEUTICALS LIMITED, Vadodara (IN)

(72) Inventors: Venkat Raman Jayaraman, Vadodara (IN); Sanjiv Tomer, Vadodara (IN); Piyush Rana, Vadodara (IN); Kamlesh Kanzariya, Vadodara (IN); Sunit Kumar, Vadodara (IN); Nilav Patel, Vadodara (IN); Manoj Borsaniya, Vadodara (IN); Sudhir Shah, Vadodara (IN); Anand Thirunavakarasu, Vadodara (IN)

( * ) Notice: Subject to any disclaimer, the term of this patent is extended or adjusted under 35 U.S.C. 154(b) by 0 days.

(21) Appl. No.: 15/304,929

(22) PCT Filed: Apr. 21, 2015

(86) PCT No.: PCT/IB2015/052904
§ 371 (c)(1),
(2) Date: Oct. 18, 2016

(87) PCT Pub. No.: WO2015/166379
PCT Pub. Date: Nov. 5, 2015

(65) Prior Publication Data
US 2017/0189394 A1     Jul. 6, 2017

(30) Foreign Application Priority Data

Apr. 28, 2014 (IN) .................. 1476/MUM/2014
Oct. 14, 2014 (IN) .................. 3288/MUM/2014

(51) Int. Cl.
*A61K 31/495* (2006.01)
*C07D 241/04* (2006.01)

(52) U.S. Cl.
CPC .......... *A61K 31/495* (2013.01); *C07D 241/04* (2013.01)

(58) Field of Classification Search
None
See application file for complete search history.

(56) References Cited

FOREIGN PATENT DOCUMENTS

| | | | | |
|---|---|---|---|---|
| CA | 2885266 A1 | 3/2014 | | |
| WO | WO-2007144005 A1 | * | 12/2007 | ......... C07D 295/096 |
| WO | WO-2013185209 A1 | * | 12/2013 | ........... C07D 405/12 |

OTHER PUBLICATIONS

Written Opinion and Search Report dated Nov. 30, 2015 for PCT International Application No. PCT/IB2015/052904.

* cited by examiner

*Primary Examiner* — Golam M Shameem
*Assistant Examiner* — Laura M Daniel
(74) *Attorney, Agent, or Firm* — Schiff Hardin LLP

(57) ABSTRACT

The present invention provides polymorphic forms of Vortioxetine of and its pharmaceutically acceptable salts. Specifically the present invention relates to the novel crystalline forms of Vortioxetine or its pharmaceutically acceptable salts. Moreover, the present invention also provides an amorphous form of Vortioxetine hydrobromide and a stable amorphous co-precipitate of Vortioxetine hydrobromide with pharmaceutically acceptable excipients.

5 Claims, 16 Drawing Sheets

Figure 1: X-ray powder diffraction pattern of Vortioxetine hydrobromide Form A.
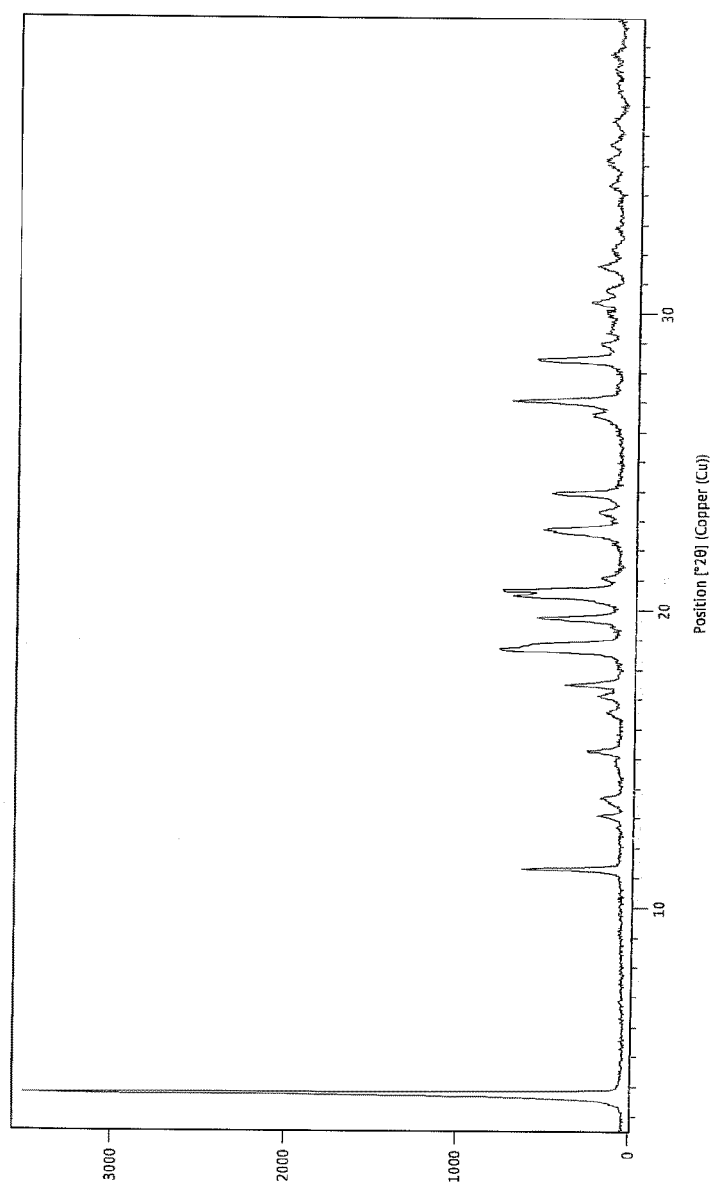

Figure 2: X-ray powder diffraction pattern of Vortioxetine hydrobromide Form Ad.
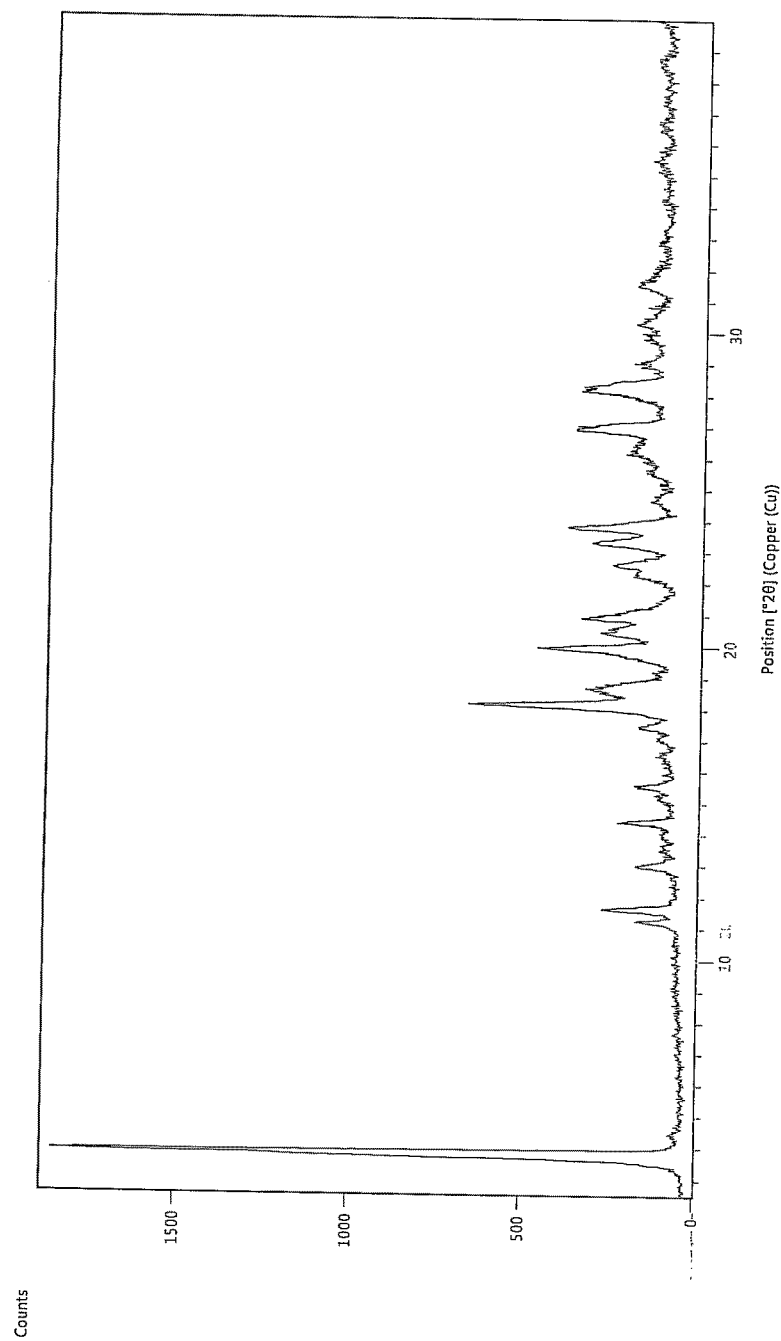

Figure 3: X-ray powder diffraction pattern of amorphous form of Vortioxetine hydrobromide.
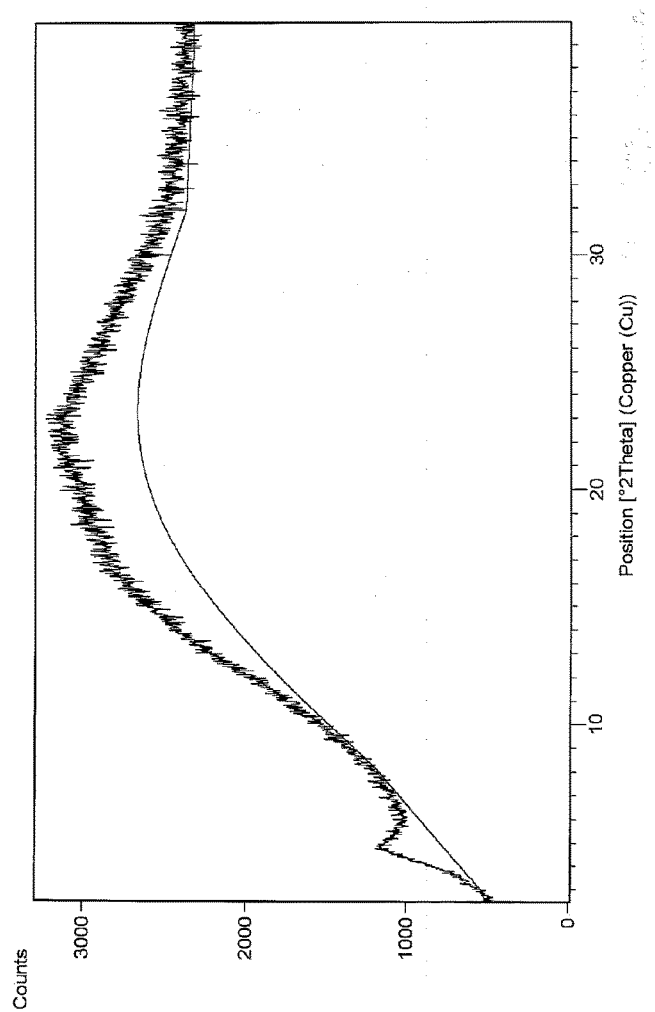

Figure 4: X-ray powder diffraction pattern of amorphous Vortioxetine hydrobromide premix with copovidone.
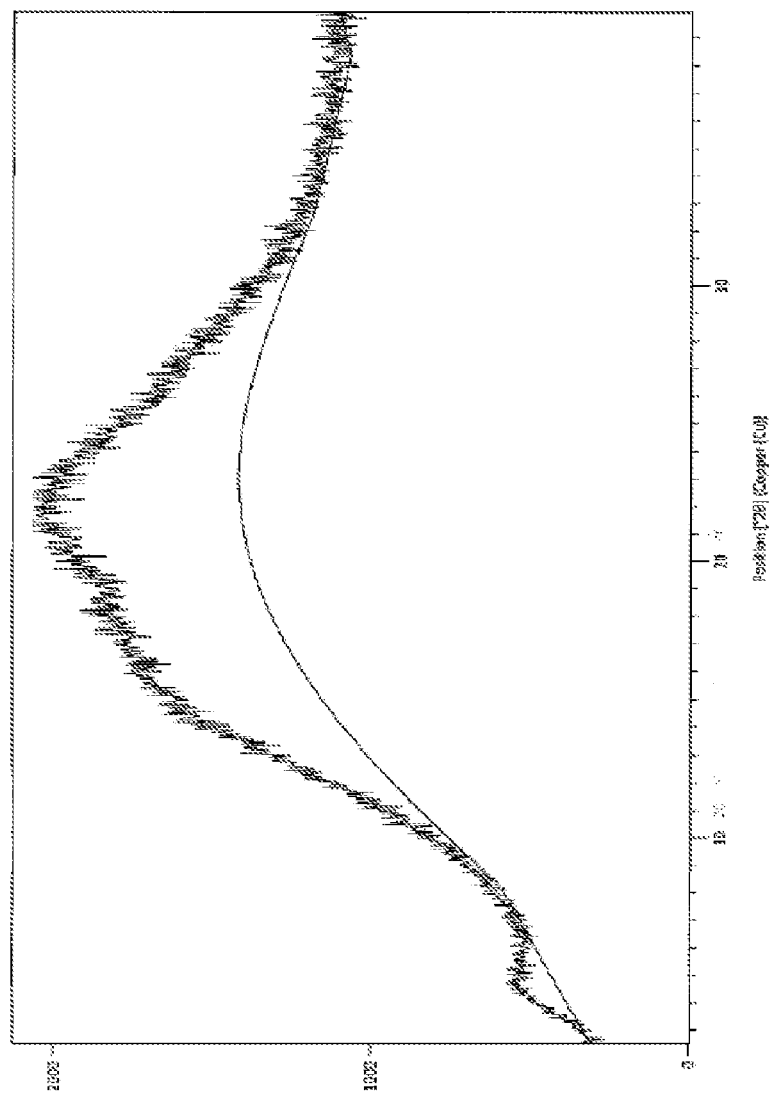

Figure 5: X-ray powder diffraction pattern novel crystalline Vortioxetine base
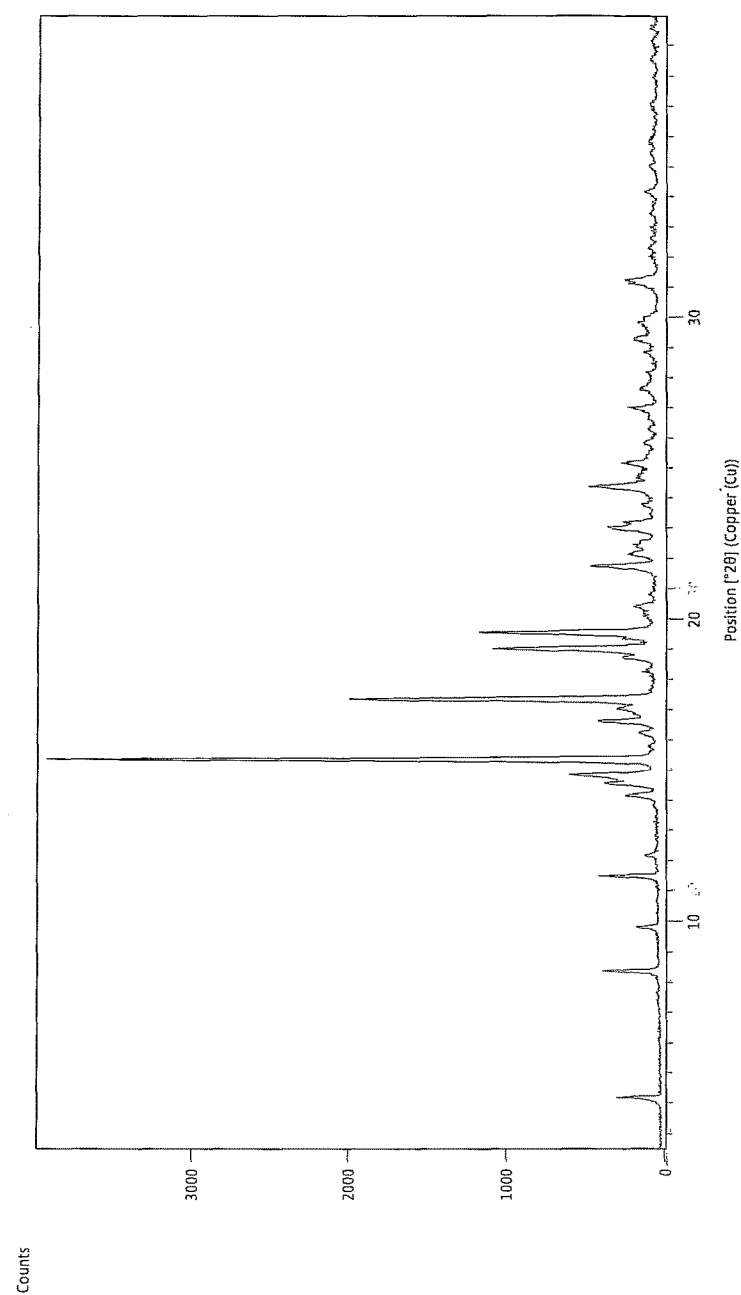

Figure 6: X-ray powder diffraction pattern of Vortioxetine hydrobromide Form B.
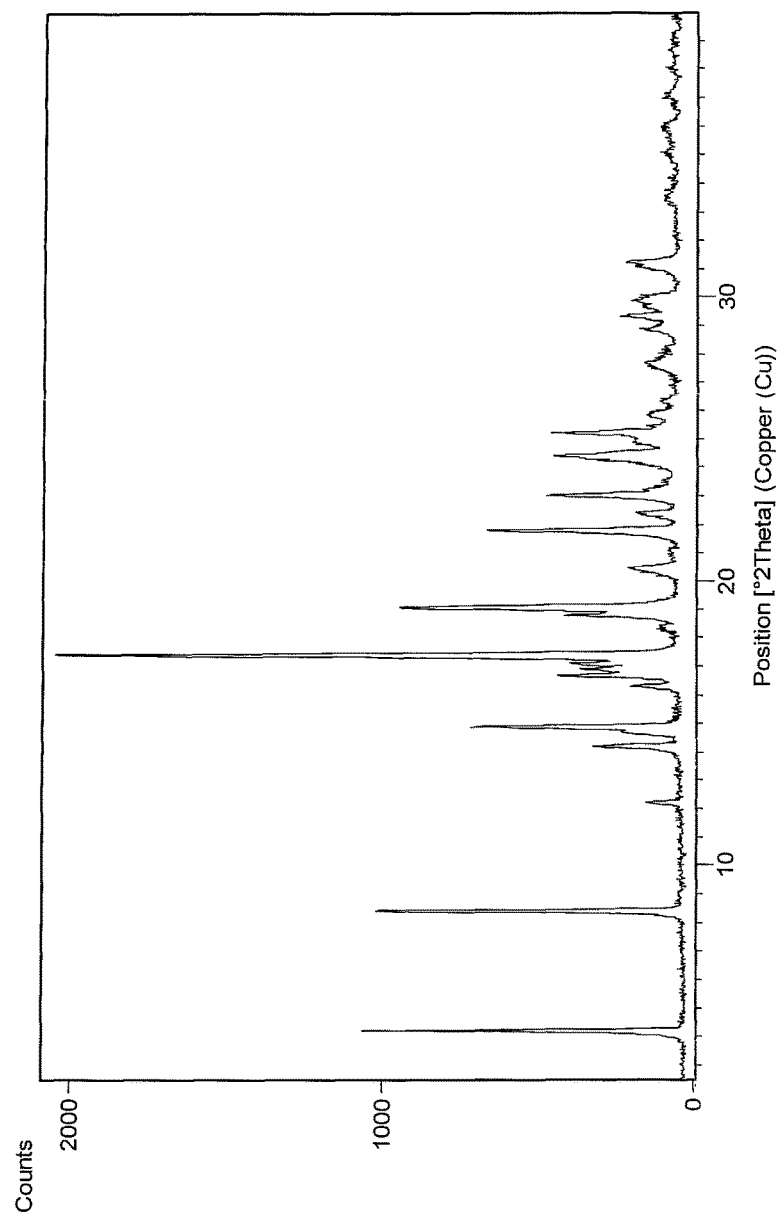

Figure 7: DSC of Vortioxetine hydrobromide form B.
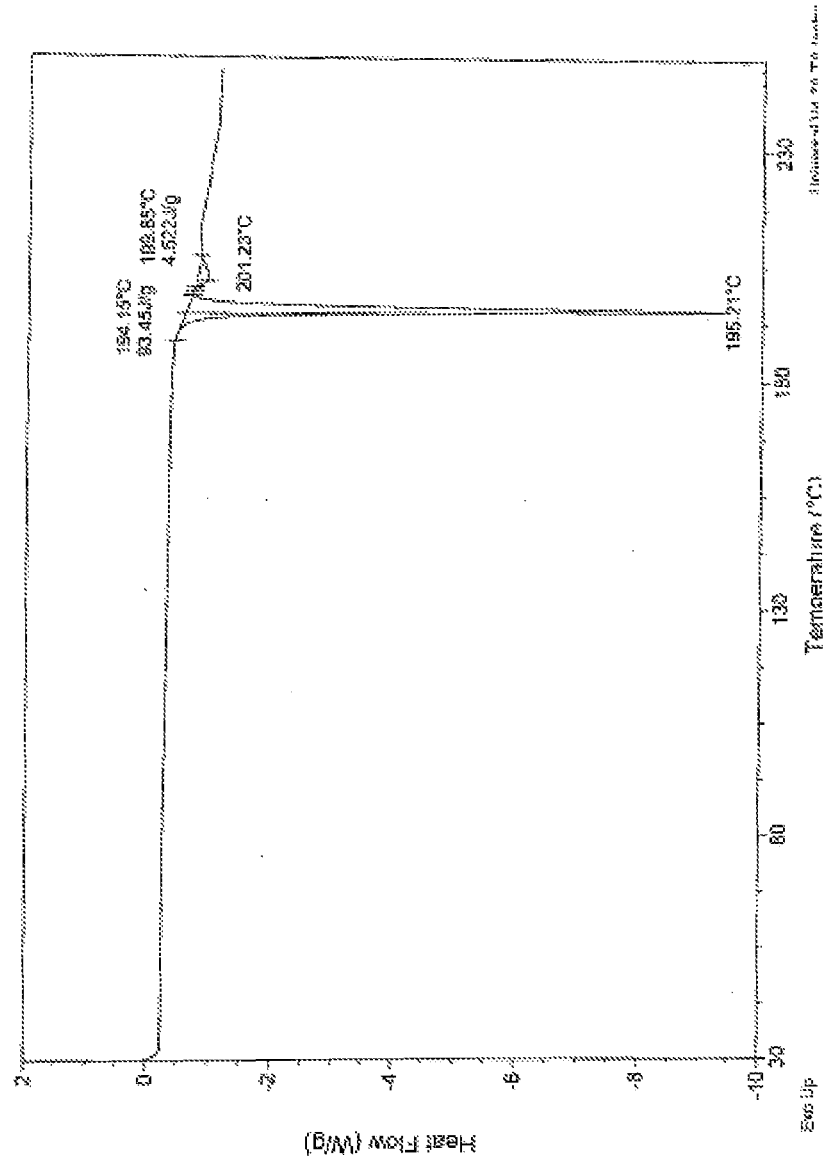

Figure 8: X-ray powder diffraction pattern of Vortioxetine hydrobromide benzyl alcohol solvate form C.
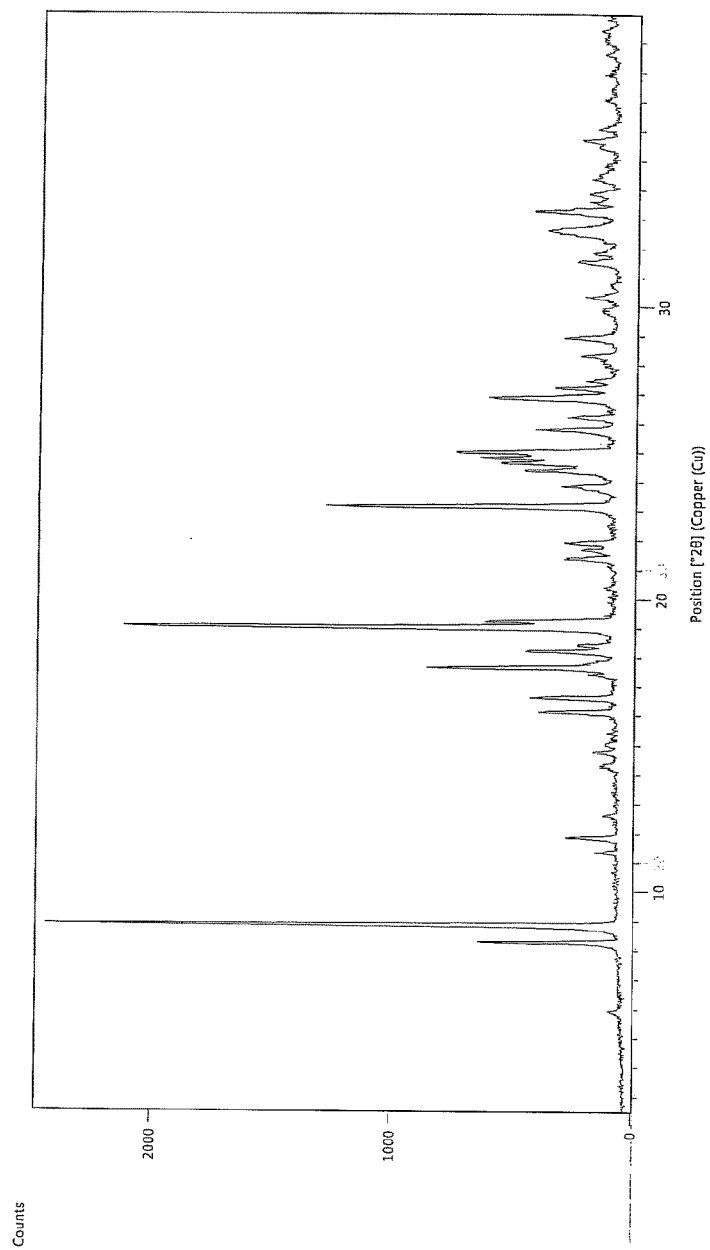

Figure 9: Fourier Transform Infrared (FTIR) spectrum of Vortioxetine hydrobromide benzyl alcohol solvate form C.
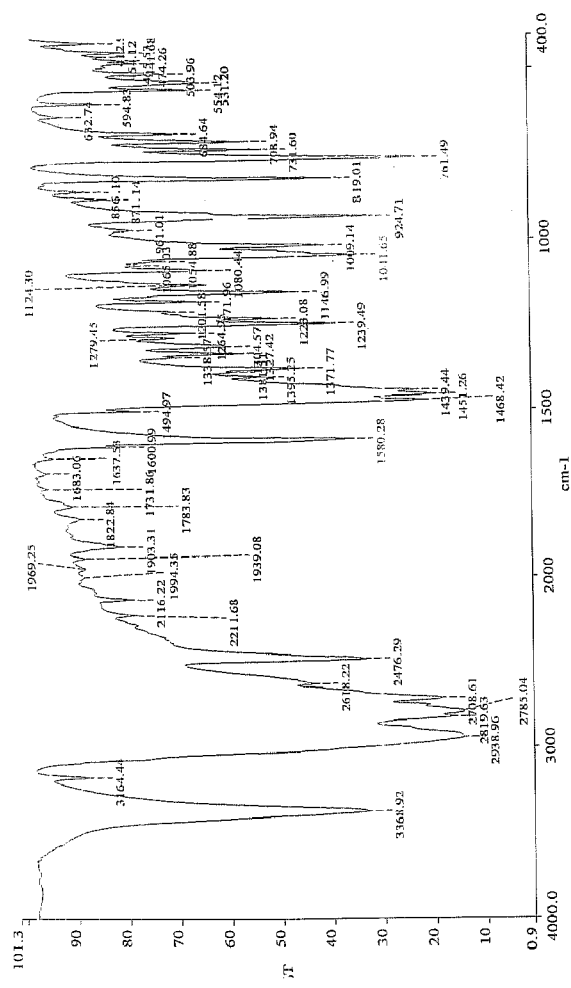

Figure 10: Thermogravimetric analyses (TGA) curve of Vortioxetine hydrobromide benzyl alcohol solvate form C.
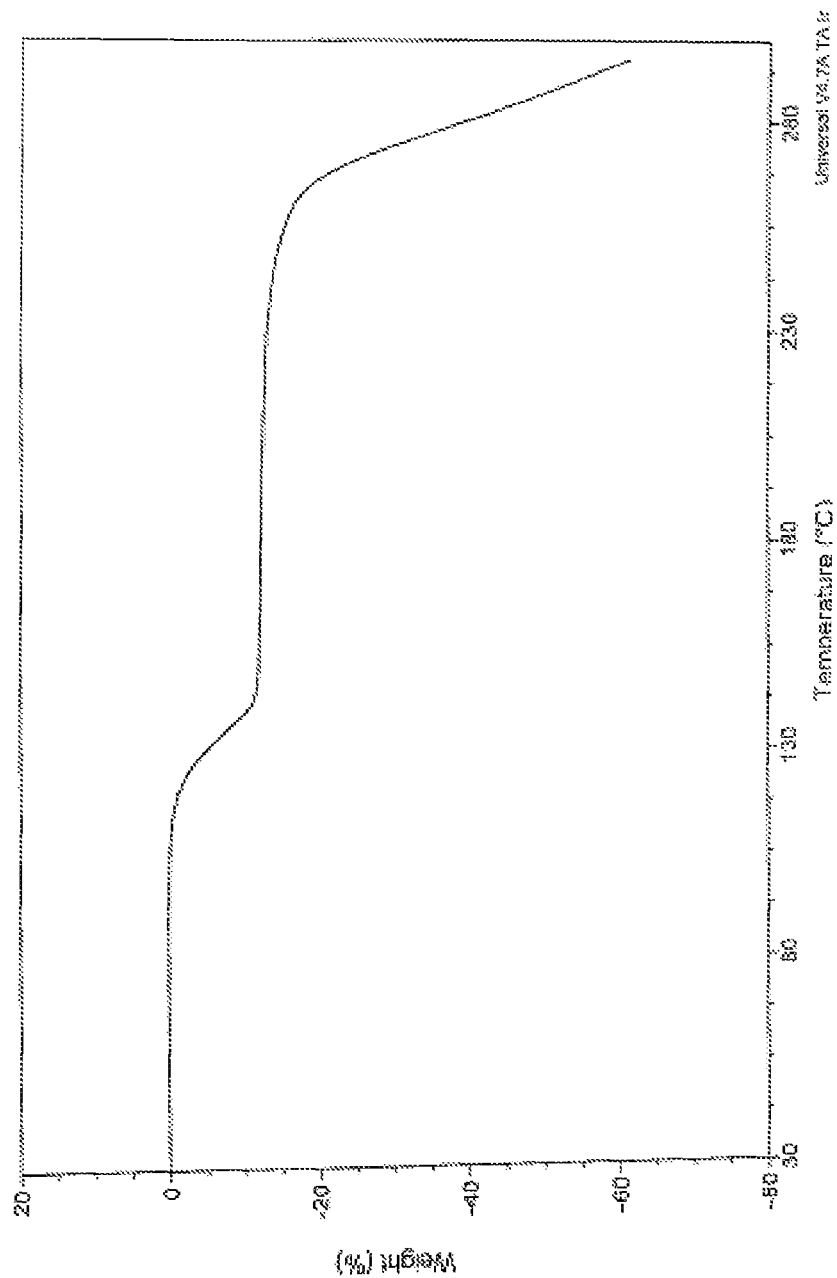

Figure 11: Differential Scanning Calorimetry (DSC) of Vortioxetine hydrobromide benzyl alcohol solvate form C.
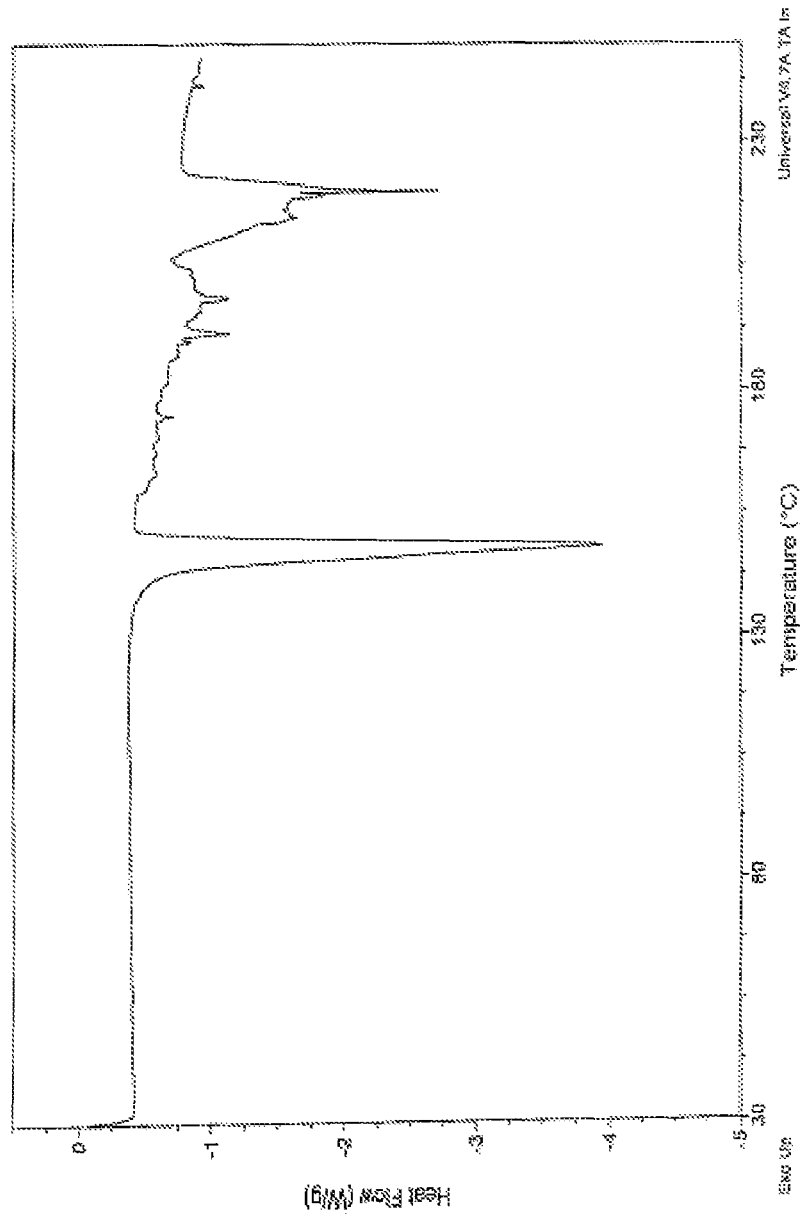

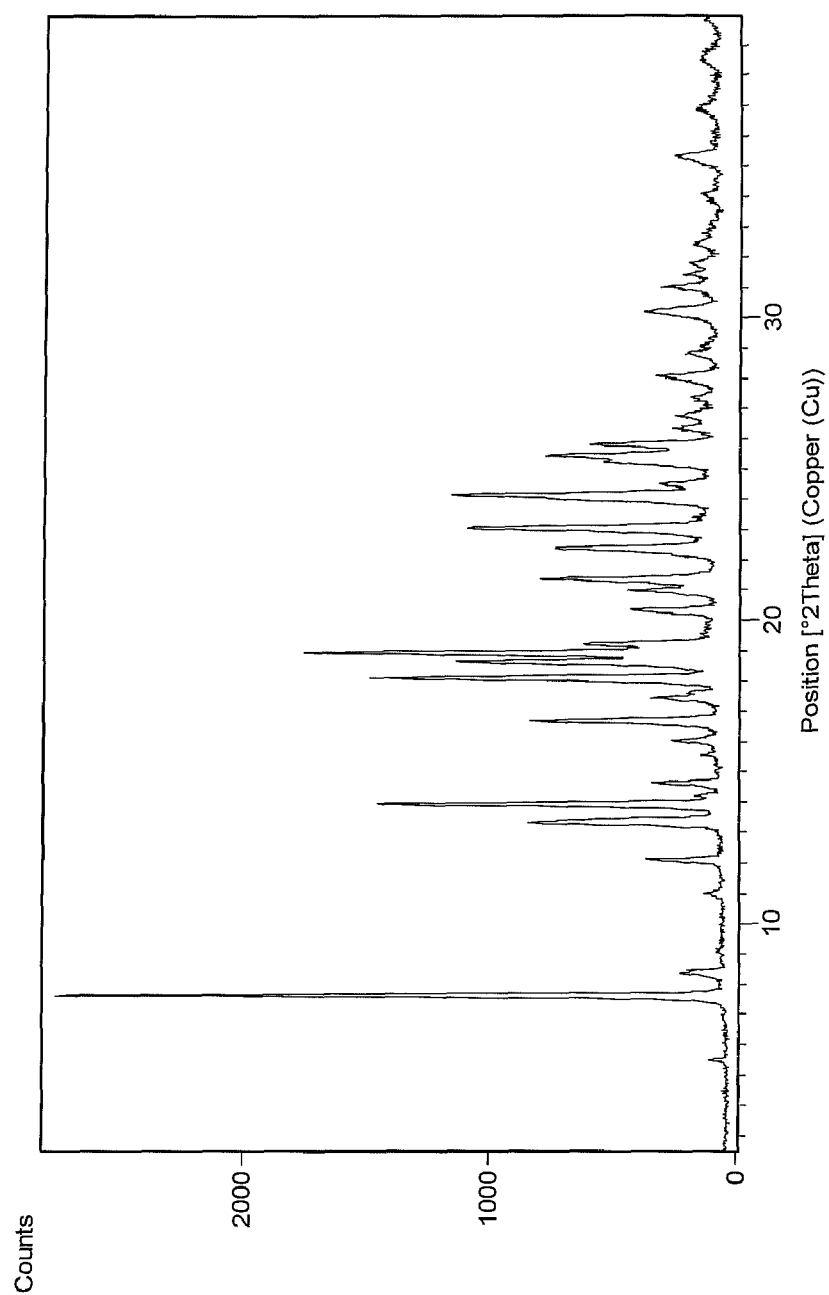
Figure 12: X-ray powder diffraction pattern of Vortioxetine adipate.

Figure 13: X-ray powder diffraction pattern of Vortioxetine malonate.
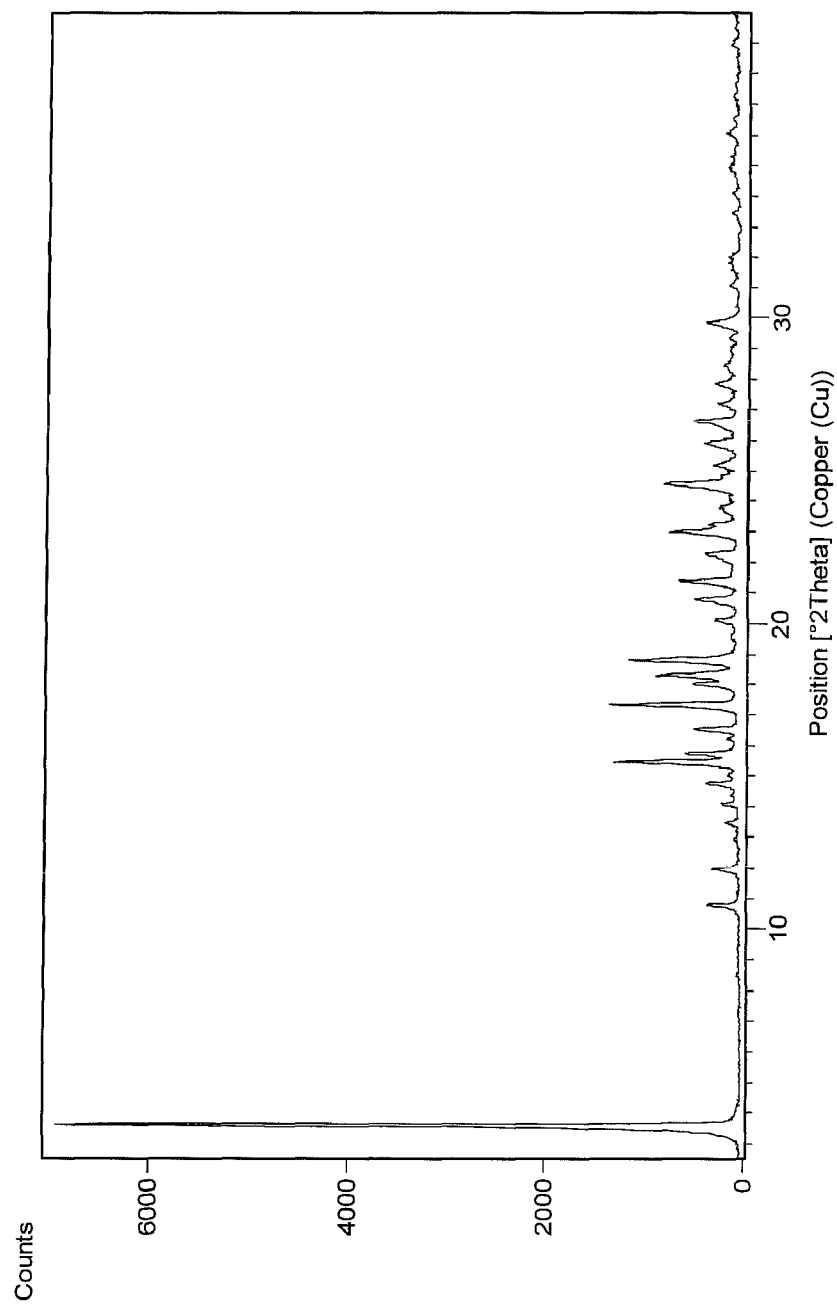

Figure 14: X-ray powder diffraction pattern of Vortioxetine pyruvate.
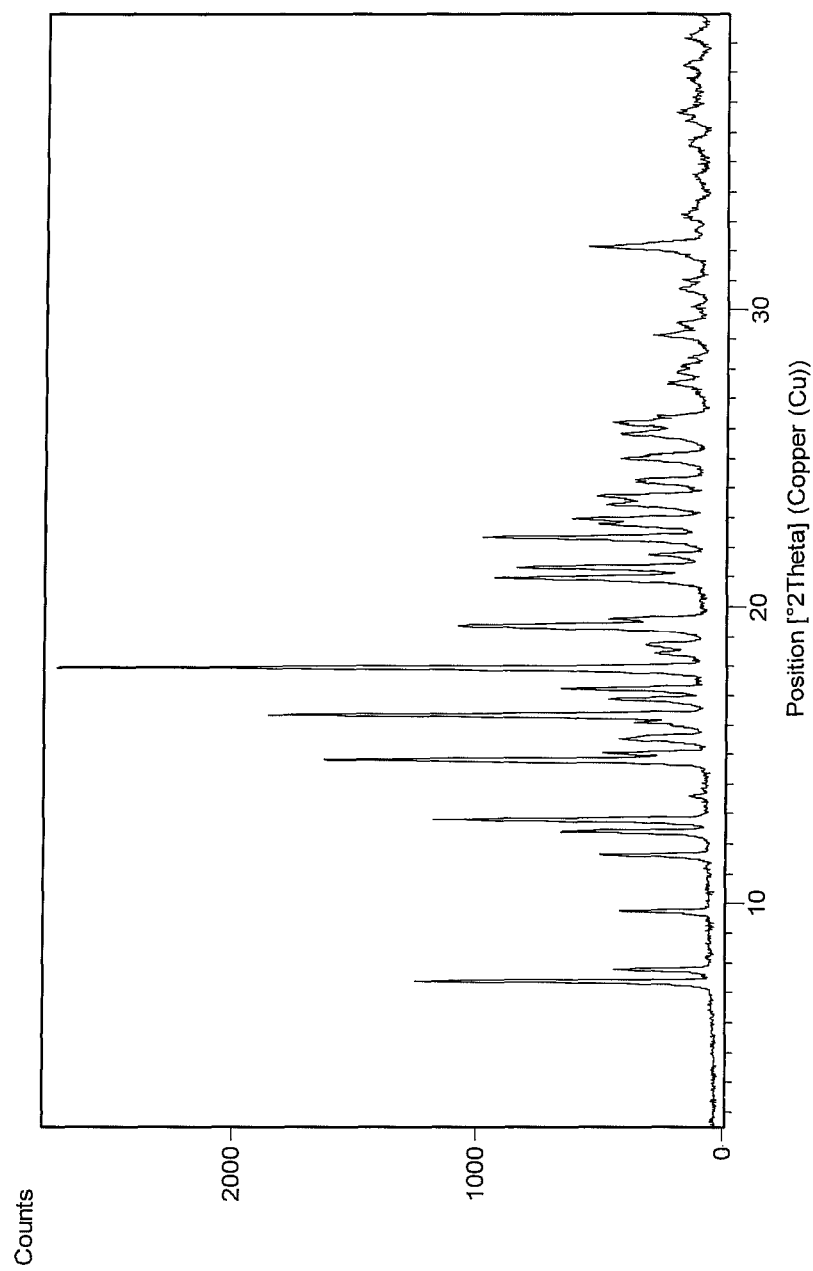

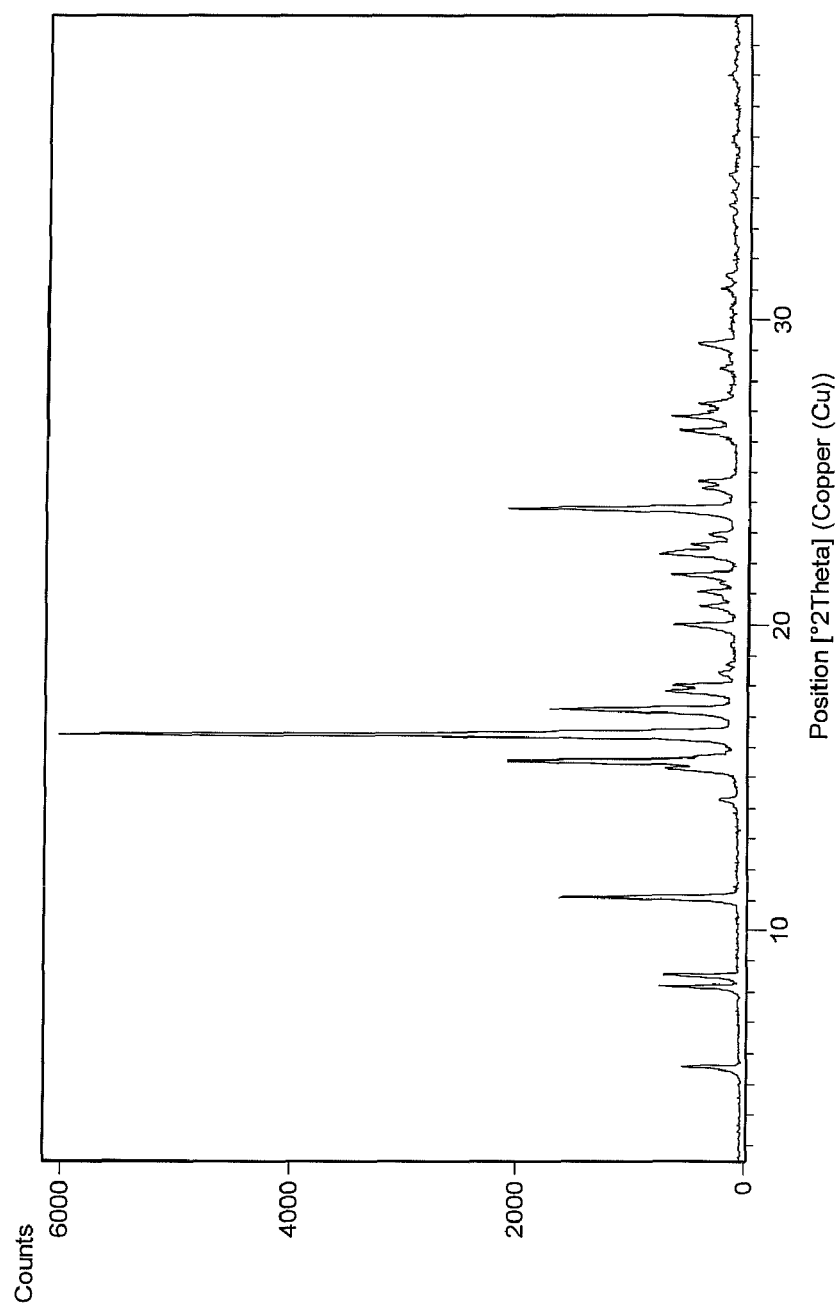
Figure 15: X-ray powder diffraction pattern Vortioxetine glutarate

Figure 16: X-ray powder diffraction pattern of Vortioxetine hydrobromide diethyl ether solvate.
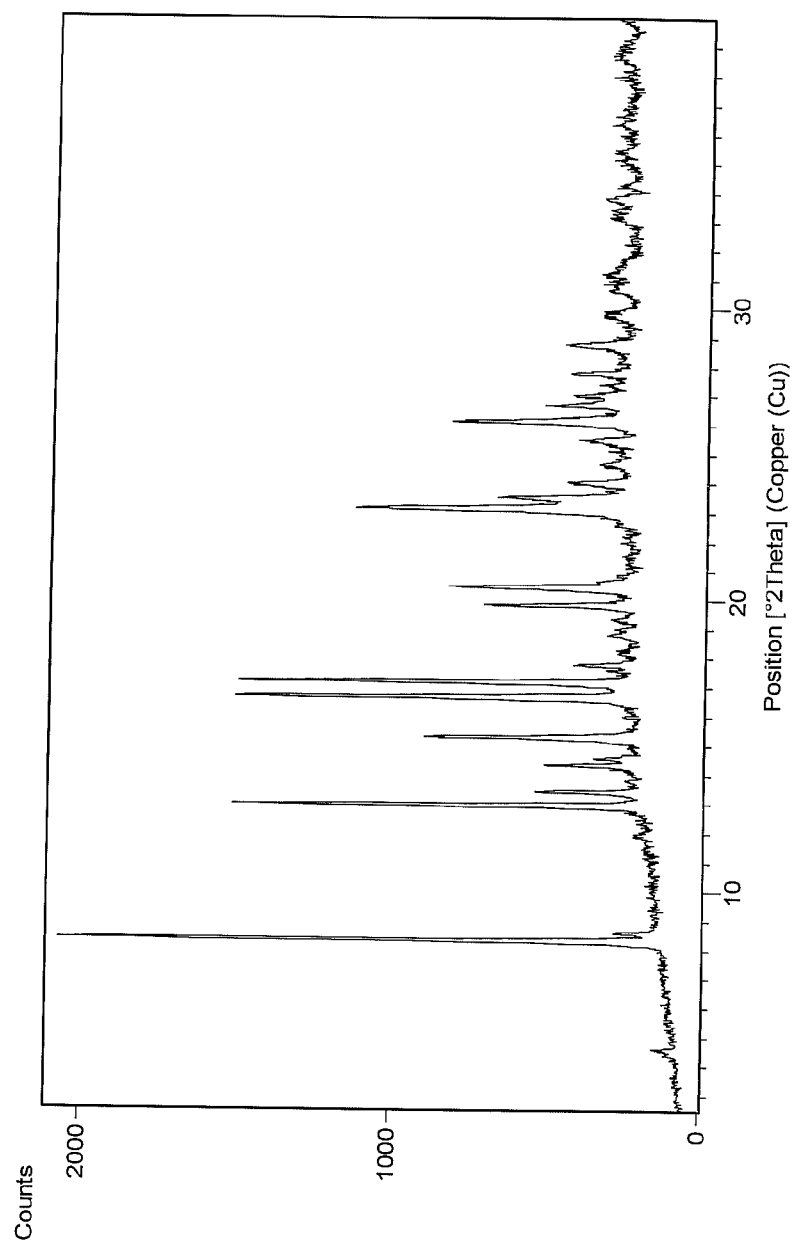

POLYMORPHIC FORMS OF VORTIOXETINE AND ITS PHARMACEUTICALLY ACCEPTABLE SALTS

RELATED APPLICATION

This application is a U.S. Section 371 national stage application based on PCT International Application No. PCT/IB2015/052904, filed on 21 Apr. 2015, which claims the benefit of priority of and to our Indian patent application numbers 1476/MUM/2014, filed on 28 Apr. 2014, and 3288/MUM/2014, filed on 14 Oct. 2014, which are all incorporated herein by reference.

FIELD OF INVENTION

The present invention provides polymorphic forms of Vortioxetine of formula-I and its pharmaceutically acceptable salts. Specifically the present invention relates to the novel crystalline forms of Vortioxetine or its pharmaceutically acceptable salts. Moreover, the present invention also provides an amorphous form of Vortioxetine hydrobromide and a stable amorphous co-precipitate of Vortioxetine hydrobromide with pharmaceutically acceptable excipients.

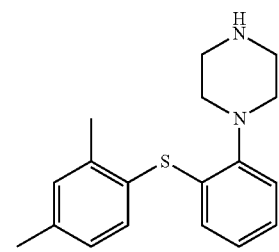

Formula I

BACKGROUND OF THE INVENTION

Vortioxetine hydrobromide is indicated for the treatment of major depressive disorder (MDD). It is a serotonin (5-HT) reuptake inhibitor, which is considered as its mechanism of action for the treatment of MDD. It is available in the market as brand name of BRINTELLIX which contains the beta (β) polymorph of Vortioxetine hydrobromide, an antidepressant.

Vortioxetine was first described in U.S. Pat. No. 7,144,884. It describes manufacturing process of Vortioxetine. It involves resin base support to prepare Vortioxetine. Process is as describe in below scheme.

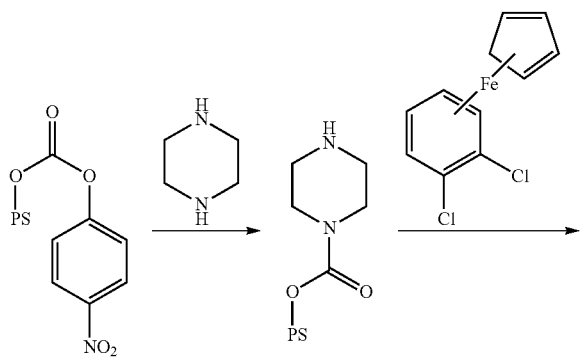

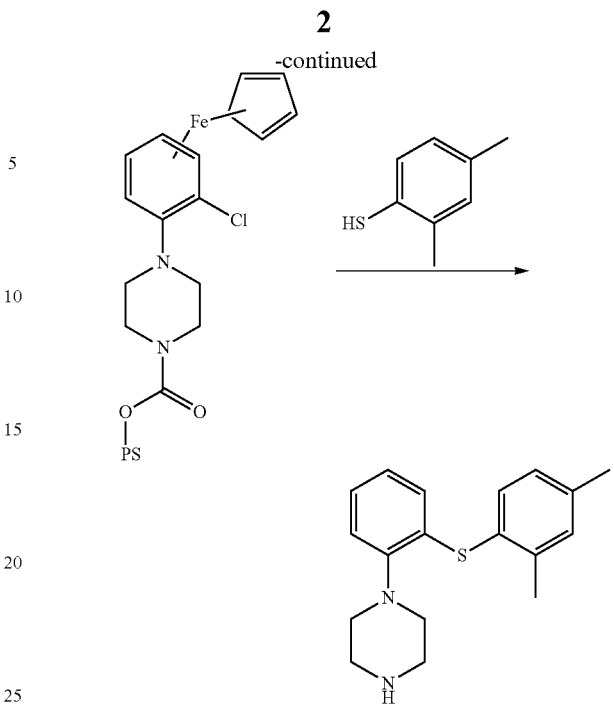

WO2007144005A1 describes manufacturing process for the preparation of Vortioxetine. The first step of it involves cross coupling reaction between 2,4-dimethylthiophenol and 2-bromoiodobenzene using Pd catalysis in presence of phosphine ligand and base which furnish I-(2-Bromo-phenylsulfanyl)-2,4-dimethylbenzene which was reacted with unprotected piperazine or protected to furnish respectively 1-[2-(2,4-Dimethyl-phenylsulfanyl)-phenyl]-piperazine or (4-[2-(2,4-Dimethyl-phenylsulfanyl)-phenyl]-BOC-piperazine). Protected BOC group was removed by HCl to produce Vortioxetine. This patent also describes one pot process for the synthesis of Vortioxetine.

WO2013102573A1 describes one pot process for the preparation of Vortioxetine. It involves a coupling reaction between 1-iodo-2,4-dimethylbenzene, 2-bromo thiophenol and piperazine in presence of Pd catalyst, phosphine ligand and base to furnish 1-[2-(2,4-Dimethyl-phenylsulfanyl)-phenyl]-piperazine.

Furthermore, WO2007144005 discloses different polymorph of Vortioxetine base and its salt. They mainly focused on crystalline base, alpha form of hydrobromide salt, beta form of hydrobromide salt, gamma form of hydrobromide salt, hemi hydrate of hydrobromide salt, the mixture of the ethyl acetate solvate and the alpha form of the hydrobromide salt, hydrochloride salt, monohydrate of hydrochloride salt, mesylate salt, fumarate salt, maleate salt, meso-tartrate salt, L-(+)-tartrate salt, D-(−)-tartrate salt, sulphate salt, phosphate salt, nitrate salt of Vortioxetine.

WO2010121621A1 discloses AH1, MH1 & MH2 form of Vortioxetine-lactate and also discloses α, β, γ and MH form of Vortioxetine DL-lactate.

WO2010094285 discloses Vortioxetine HBr isopropanol solvate.

WO2014044721 discloses delta form of Vortioxetine HBr.

WO2014177491 discloses amorphous form of Vortioxetine hydrobromide with an adsorbent.

The acceptable amount of solvents in an active pharmaceutical ingredient is strictly regulated e.g. by the ICH guideline for residual solvents. Solvates of Vortioxetine hydrobromide such as e.g. the ethyl acetate solvate of WO 2007/144005 A1 and the isopropanol solvate of WO 2010/094285 A1 are no suitable crystalline forms for the preparation of a medicament as they clearly exceed the recommended solvent amount for class 3 solvents. In summary, solvates of Vortioxetine hydrobromide know in the art are no suitable forms for the preparation of a medicament due to the strict limits for residual solvents in an active pharmaceutical ingredient.

Polymorphism is defined as "the ability of a substance to exist as two or more crystalline phases that have different arrangement and/or conformations of the molecules in the crystal Lattice. Polymorphic forms of a compound can be distinguished in the laboratory by analytical methods such as X-ray diffraction (XRD), Differential Scanning Calorimetry (DSC) and Infrared spectrometry (IR).

A polymorphic form may be referred to herein as being characterized by graphical data "as shown in" a Figure. Such data include, for example, powder X-ray diffractograms. In any event, the skilled person will understand that such graphical representations of data may be subject to small variations, e.g., in peak relative intensities and peak positions due to factors such as variations in instrument response and variations in sample concentration and purity, which factors are well known to the skilled person.

The technical problem underlying the present invention is to circumvent the drawbacks of the known crystalline forms of Vortioxetine hydrobromide disclosed in the state of the art such as toxicity issues of solvates, stability issues due to water uptake, bioavailability issues due to limited solubility and preparation issues due to similar crystallization processes by providing novel polymorphic forms of Vortioxetine and its pharmaceutically acceptable salts which shows high solubility and is obtained in polymorphically pure form in an easy and reliable manner.

SUMMARY OF THE INVENTION

The present inventors have focused on the problems associated with the prior art polymorphs and have invented several novel polymorphic forms of Vortioxetine and its pharmaceutically acceptable salts.

In one aspect, the present invention provides a novel crystalline form-A of Vortioxetine hydrobromide and process of making thereof.

In another aspect, the present invention provides a novel crystalline form Ad of Vortioxetine hydrobromide and process of making thereof.

In another aspect, the present invention provides a novel crystalline form of Vortioxetine base.

In another aspect, the present invention provides an improved process for the preparation of beta crystalline form of Vortioxetine hydrobromide.

In another aspect, the present invention provides an amorphous form of Vortioxetine hydrobromide and process of making thereof.

In another aspect, the present invention provides a stable amorphous co-precipitate of Vortioxetine hydrobromide having enhanced stability, dissolution properties that can be easily formulated into pharmaceutical compositions and process of making thereof.

In another aspect, the present invention provides a novel crystalline form B of Vortioxetine hydrobromide.

In another aspect present invention also relates to a novel crystalline benzyl alcohol solvate of Vortioxetine hydrobromide form C and process for making thereof.

In another aspect, the present invention provides a purification process for preparation of Vortioxetine hydrobromide using acid base treatment.

In another aspect, the present invention provides a crystalline Vortioxetine adipate.

In another aspect, the present invention provides an improved process for preparing known crystalline form beta (β).

BRIEF DESCRIPTION OF DRAWINGS

FIG. 1: X-ray powder diffraction pattern of Vortioxetine hydrobromide Form A.

FIG. 2: X-ray powder diffraction pattern of Vortioxetine hydrobromide Form Ad.

FIG. 3: X-ray powder diffraction pattern of amorphous form of Vortioxetine hydrobromide.

FIG. 4: X-ray powder diffraction pattern of amorphous Vortioxetine hydrobromide premix with copovidone.

FIG. 5: X-ray powder diffraction pattern novel crystalline Vortioxetine base.

FIG. 6: X-ray powder diffraction pattern of Vortioxetine hydrobromide Form B.

FIG. 7: DSC of Vortioxetine hydrobromide form B.

FIG. 8: X-ray powder diffraction pattern of Vortioxetine hydrobromide benzyl alcohol solvate form C.

FIG. 9: Fourier Transform Infrared (FTIR) spectrum of Vortioxetine hydrobromide benzyl alcohol solvate form C.

FIG. 10: Thermo gravimetric analyses (TGA) curve of Vortioxetine hydrobromide benzyl alcohol solvate form C.

FIG. 11: Differential Scanning Calorimetry (DSC) of Vortioxetine hydrobromide benzyl alcohol solvate form C.

FIG. 12: X-ray powder diffraction pattern of Vortioxetine adipate.

FIG. 13: X-ray powder diffraction pattern of Vortioxetine malonate.

FIG. 14: X-ray powder diffraction pattern of Vortioxetine pyruvate.

FIG. 15: X-ray powder diffraction pattern Vortioxetine glutarate.

FIG. 16: X-ray powder diffraction pattern of Vortioxetine hydrobromide diethyl ether solvate.

DETAILED DESCRIPTION OF INVENTION

The present invention provides novel polymorphic forms of Vortioxetine and its pharmaceutically acceptable salts. These solid state forms can be used to prepare formulations thereof.

In one embodiment the present invention provides a process of preparation of Vortioxetine of formula-I or pharmaceutically acceptable salts comprising the steps of

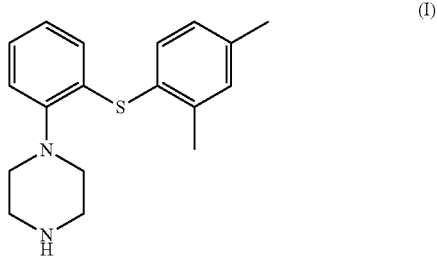 [SMILES: Cc1ccc(Sc2ccccc2N2CCNCC2)c(C)c1]

a. reacting 2,4-dimethyl thiophenol and o-fluoro nitro benzene in presence of suitable base and suitable solvent to provide compound of formula II.

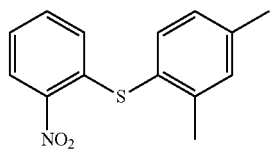

(II)

b. reducing compound of formula II using suitable reducing agent to prepare compound of formula III.

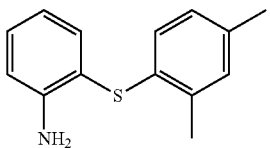

(III)

c. converting compound of formula III into Vortioxetine.

Reacting 2,4-dimethyl thiophenol and o-fluoro nitro benzene can be performed in the presence of suitable base which are one or more of organic or inorganic bases selected from the group of alkali or alkaline earth metal hydroxide, carbonate, bicarbonate, for example, NaH, NaOH, KOH, LiOH, NaHCO$_3$, KHCO$_3$, LiHCO$_3$, Na$_2$CO$_3$, K$_2$CO$_3$, Li$_2$CO$_3$, Mg(OH)$_2$, Ca(OH)$_2$, CaCO$_3$, MgCO$_3$, Ba(OH)$_2$, Be(OH)$_2$, BaCO$_3$, SrCO$_3$ and the like or mixtures thereof; primary, secondary and tertiary amines, such as pyridine, piperidine, triethylamine, diisopropyl ethyl amine, N-methyl morpholine, dimethyl amino pyridine and the like; ammonia and ammonium salts.

Reacting 2,4-dimethyl thiophenol and o-fluoro nitro benzene can be performed in the presence of suitable solvent. The term "solvent" includes any solvent or solvent mixture, including, for example, water, esters, alkanols, halogenated hydrocarbons, ketones, ethers, nitriles, polar aprotic solvents, or mixtures thereof. The esters may include one or more of ethyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of halogenated hydrocarbons include dichloromethane, chloroform, and 1,2-dichloroethane. Examples of ketones include acetone, methyl ethyl ketone, and the like. Examples of ethers include diethyl ether, tetrahydrofuran, and the like. Examples of nitriles include acetonitrile, benzonitrile. A suitable polar aprotic solvent includes one or more of N,N-dimethylformamide, N,N-dimethylacetamide, dimethylsulphoxide, N-methylpyrrolidone, sulfolane and dimethyl propylene urea.

Reacting 2,4-dimethyl thiophenol and o-fluoro nitro benzene can be performed preferably at a temperature of from 20° C. to the reflux temperature for a time period sufficient to complete the reaction, preferably for about 30 minutes to 20 hours.

After the completion of the reaction, the compound of Formula II can be isolated by a common isolation technique, such as cooling, extraction, one or more of washing, crystallization, precipitation, filtration, filtration under vacuum, decantation and centrifugation, or a combination thereof. The isolated compound of Formula II may be further purified by salt formation, crystallization or chromatographic methods, or a combination thereof. After the completion of the reaction one can go in to the next step without isolation of compound of formula II also.

The compound of Formula II is a suitable intermediate for the preparation of Vortioxetine.

The reducing agent selected from borane complexes, metals such as iron, tin, zinc; transition metals such as palladium-carbon, platinum oxide, Raney nickel in presence of hydrogen or hydrogen source selected from ammonium formate, sodium dihydrogen phosphate, hydrazine; for example, Fe—NH4Cl, Fe—HCl, Fe—CaCl2, Sn—HCl, NaHS, Zn—AcOH, Pd/C—H2, hydrazine hydrate-Raney Ni, NaBH4-NiCl2.6H2O, Ni(OAc)2.4H2O, CoCl2 likes metals, metal halides or metal Salts in a solvent including, for example, water, esters, alkanols, halogenated hydrocarbons, ketones, ethers, nitriles, polar aprotic solvents, or mixtures thereof. The esters may include one or more of ethyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of halogenated hydrocarbons include dichloromethane, chloroform, and 1,2-dichloroethane. Examples of ketones include acetone, methyl ethyl ketone, and the like. Examples of ethers include diethyl ether, tetrahydrofuran, and the like. Examples of nitriles include acetonitrile, benzonitrile and the like. A suitable polar aprotic solvent includes one or more of N,N-dimethylformamide, N,N-dimethylacetamide, dimethylsulphoxide, acetonitrile and N-methylpyrrolidone.

The reduction is carried out under a suitable reaction temperature for suitable reaction time. The reaction temperature is preferably from room temperature to below 100° C., and the reaction time is generally from 1 hour to several days. Preferred reaction conditions are disclosed in detail in the examples.

After the reduction is completed the reaction solution is treated and worked up in a usual way, e.g. by filtering off the solid components, evaporating the filtrate and/or crystallizing the amino compound or convert into suitable salt using acid. It can also purify using acid base treatment.

In one more embodiment the present invention provides a process for preparing Vortioxetine comprising the steps of converting compound of formula III in to Vortioxetine using Bis (2-chloroethyl) amine hydrochloride or Bis (2-bromoethyl) amine hydrobromide in presence of suitable solvent and optionally with acid catalyst.

Suitable solvent is selected from water, alcohols, ketones, diols, triols, esters, amides, ethers, hydrocarbons, polar aprotic solvents, polar solvents, chloro solvents, nitriles or mixtures thereof. Polar aprotic solvents such as acetone, DMF, acetonitrile, DMSO, sulfolane; alcohols such as methanol, ethanol, propanol, butanol, glycerol, propylene glycol; polyglycols such as polyethylene glycol 200, polyethylene glycol 300 and polyethylene glycol 400; pyrrolidones such as N-methyl pyrrolidone and 2-pyrrolidone; glycol ethers such as propylene glycol monomethyl ether, dipropylene glycol monomethyl ether and diethylene glycol ethyl ether, N,N,-dimethyl acetamide, PEG 300, propylene glycol; chloro solvents like methylene chloride, chloroform and ethylene chloride; hydrocarbon solvents like toluene, xylene, heptane, cyclohexane and hexane.

Acid catalyst is one selected from the group consisting of p-toluene sulfonic acid, methane sulfonic acid, nitric acid, sulphuric acid, hydrochloric acid and mixtures thereof.

This reaction is carried out under a suitable reaction temperature for suitable reaction time; preferably at a temperature of from 20° C. to the reflux temperature for a time period sufficient to complete the reaction, preferably for about 30 minutes to several days.

The embodiments of present invention are shown in below given scheme-I.

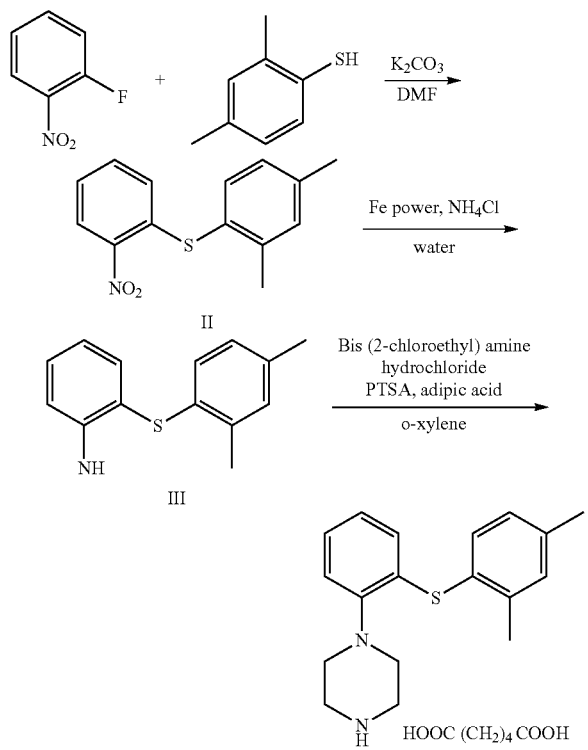

In another embodiment, the present invention provides a purification process for preparation of Vortioxetine hydrobromide using acid base treatment.

In another embodiment, the present invention provides a process for purification of Vortioxetine comprising;
a. treating of the Vortioxetine base with a suitable acid;
b. isolating the acid addition salt of Vortioxetine; and
c. treating acid addition salt of Vortioxetine with a suitable base to provide highly pure Vortioxetine.

Wherein, the suitable acid is selected from organic acids like acetic acid, citric acid, para toluene sulfonic acid, malic acid, succinic acid, adipic acid, pyruvic acid, malonic acid, glutaric acid, trifluoroacetic acid, camphoric acid, napthalene sulfonic acid, isethionic acid, camphor sulfonic acid and the like; the suitable base is selected from hydroxides and carbonates of alkali metals or ammonia; the suitable solvent is selected from water, hydrocarbon solvents, halogenated solvents, alcoholic solvents, polar-aprotic solvents, ketone solvents and/or their mixtures thereof;

In another embodiment the present invention provides Vortioxetine acid addition salts in crystalline form and process for making them, which comprise:
a) providing a solution of Vortioxetine free base in a suitable solvent or a mixture of solvents capable of dissolving Vortioxetine;
b) mixing with the solution of organic acid dissolved in the suitable solvent;
c) optionally, filtering the solvent solution to remove any extraneous matter; and
d) isolating acid addition salt of Vortioxetine.

Yet, another embodiment of the present invention is to provide pure crystalline Vortioxetine adipate salt, Vortioxetine malonate salt, Vortioxetine pyruvate salt and Vortioxetine glutarate salt.

In another embodiment present invention provides a crystalline Vortioxetine adipate. A crystalline form of Vortioxetine adipate having an X-ray powder diffractogram comprising peaks at 2-theta angles of 7.62±0.2°, 12.08±0.2°, 13.35±0.2°, 13.93±0.2° and 14.61±0.2°. The crystalline Vortioxetine adipate has XPRD pattern as shown in FIG. 12. In another embodiment present invention provides process for preparation of Vortioxetine adipate comprising the step of treatment of Vortioxetine with adipic acid.

In another embodiment present invention also provides crystalline forms of Vortioxetine malonate. A crystalline form of Vortioxetine malonate having an X-ray powder diffractogram comprising peaks at 2-theta angles of 10.78±0.2°, 11.97±0.2°, 14.57±0.2°, 15.44±0.2° and 15.72±0.2°. A crystalline Vortioxetine malonate has XPRD pattern as shown in FIG. 13.

In another embodiment present invention also provides crystalline Vortioxetine pyruvate. A crystalline form of Vortioxetine pyruvate having an X-ray powder diffractogram comprising peaks at 2-theta angles of 7.39±0.2°, 12.81±0.2°, 14.82±0.2°, 16.33±0.2° and 17.94±0.2°. A crystalline Vortioxetine pyruvate has XPRD pattern as shown in FIG. 14.

In another embodiment present invention also provides crystalline Vortioxetine glutarate. A crystalline form of Vortioxetine glutarate having an X-ray powder diffractogram comprising peaks at 2-theta angles of 11.10±0.2°, 15.53±0.2°, 16.14±0.2°, 17.24±0.2° and 23.79±0.2°. A crystalline Vortioxetine glutarate has XPRD pattern as shown in FIG. 15.

In another embodiment the present invention provides a novel, pure and stable amorphous form of Vortioxetine Hydrobromide characterized by X-ray diffraction pattern as depicted in FIG. 3.

In another embodiment of the present invention, a process is provided for preparation of a stable and substantially pure amorphous form of Vortioxetine Hydrobromide, which comprises:
a) providing a solution of Vortioxetine Hydrobromide in a suitable solvent or a mixture of solvents capable of dissolving Vortioxetine Hydrobromide;
b) optionally, filtering the solvent solution to remove any extraneous matter; and
c) substantially removing the solvent from the solution to afford amorphous form of Vortioxetine Hydrobromide.

The solution of Vortioxetine Hydrobromide can be obtained by the known methods that include direct use of a reaction mixture containing Vortioxetine Hydrobromide that is obtained in the course of its synthesis, or dissolving Vortioxetine Hydrobromide in a suitable solvent or mixture of solvents.

Suitable solvents in all process may include but are not limited to water; alcohols such as methanol, ethanol, isopropanol, 2-propanol, 1-butanol, t-butyl alcohol, 1-pentanol, 2-pentanol, amyl alcohol, ethylene glycol, glycerol and the like; ketones such as acetone, butanone, 2-pentanone, 3-pentanone, methyl butyl ketone, methyl isobutyl ketone, and the like; esters such as ethyl formate, methyl acetate, ethyl acetate, propyl acetate, t-butyl acetate, isobutyl acetate, hydrocarbons like toluene, xylene, methylene dichloride, ethylene dichloride, chlorobenzene, and the like, nitriles like acetonitrile, ethers like diethyl ether, diisopropyl ether, t-butyl methyl ether, dibutyl ether, tetrahydrofuran, 1,4-dioxane, 2-methoxyethanol. Polar aprotic solvents like N,N-dimethylformamide, N,N-dimethylacetamide, N-methylpyrrolidone, pyridine, dimethylsulfoxide, sulfolane, formamide, acetamide, propanamide, pyridine, formic acid, acetic acid, propionic acid and the like; and mixtures thereof.

The process can produce amorphous Vortioxetine Hydrobromide in substantially pure form. The term "substantially pure amorphous form of Vortioxetine Hydrobromide" refers to the amorphous form of Vortioxetine Hydrobromide having purity greater than about 98%, specifically greater than about 99%, more specifically greater than about 99.5% and still more specifically greater than about 99.9% (measured by HPLC).

The amorphous Vortioxetine Hydrobromide obtained by the process disclosed herein is consistently reproducible and has good flow properties, and which is particularly suitable for bulk preparation and handling, and so, the amorphous Vortioxetine Hydrobromide obtained by the process disclosed herein is suitable for formulating Vortioxetine Hydrobromide.

Removal of solvent in step-(c) is accomplished by, for example, substantially complete evaporation of the solvent, concentrating the solution and filtering the solid under inert atmosphere. Alternatively, the solvent may also be removed by evaporation.

Evaporation can be achieved at sub-zero temperatures by the lyophilisation or freeze-drying technique. The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying.

In one more embodiment, the present invention provides Vortioxetine Hydrobromide co-precipitate having enhanced stability and dissolution properties and process for preparation thereof.

The term "co-precipitate" herein refers to a composition prepared by dissolving a Vortioxetine hydrobromide in an organic solvent or mixture of organic solvents with one or more pharmaceutically acceptable carriers and converting the solution to a solid form.

In one more embodiment, the present invention provides an amorphous co-precipitate of Vortioxetine Hydrobromide with pharmaceutically acceptable excipients wherein the pharmaceutically acceptable excipients may be one or more selected from copovidone, povidone, ethyl cellulose, hydroxypropyl methylcellulose, polyethylene glycol, soluplus, starch, microcrystalline cellulose, crosspovidone, methylcellulose, cellulose ethers, sodium carboxymethylcellulose, dextrose, lactose, sucrose, sorbitol, mannitol, polyvinylpyrrolidone, polyacrylamides, polyvinyloxoazolidone, polyvinylalcohols, carmellose, carmellose sodium, glycerol monosterate or starch.

In an embodiment, a pharmaceutical composition comprising a therapeutically effective amount of an amorphous co-precipitate of Vortioxetine Hydrobromide and one or more pharmaceutically acceptable carriers, excipients, or diluents.

In one more embodiment a process for preparation of a stable amorphous co-precipitate of Vortioxetine hydrobromide comprising the steps of:

a) preparing a solution comprising a mixture of Vortioxetine hydrobromide and one or more pharmaceutically acceptable excipients;
b) removing the solvent to obtain amorphous co-precipitate of Vortioxetine hydrobromide in combination with a pharmaceutically acceptable excipients.

In an embodiment, the present invention provides a stable amorphous co-precipitate of Vortioxetine Hydrobromide having enhanced stability, dissolution properties that can be easily formulated into pharmaceutical compositions.

According to present invention, the ratio of Vortioxetine Hydrobromide to excipients is in a range of 1:0.1 to 1:10.

The suitable excipients of step (a) can be any pharmaceutically acceptable excipient(s) discussed in the specification includes but not limited to diluents, lubricants, disintegrants, glidants, stabilizers & surface active agents or mixtures thereof.

Exemplary pharmaceutically acceptable excipients include, but are not limited to starch, pregelatinized starch, lactose, mannitol, sorbitol, xylitol, sucrose, dextrates, dextrin, dextrose, microcrystalline cellulose, powdered cellulose, calcium carbonate, calcium sulfate, dibasic calcium phosphate, tribasic calcium phosphate, alginic acid, sodium alginate, crosspovidone, sodium starch glycolate, crosscarmellose, methylcellulose, cellulose ethers, sodium carboxymethylcellulose, ethylcellulose, polyethylene glycol, polyvinylpyrrolidone, pectins, gelatin, polyacrylamides, polyvinyloxoazolidone, polyvinylalcohols, polyvinyl pyrrolidone (PVP), polyethylene glycol (PEG), pectin, pullulan, mannan, gelatin, gum arabic, a cyclodextrin, agar, a polyoxysorbitan fatty acid ester, an alginate or cellulose derivatives, hypromellose (HPMC), hydroxypropyl cellulose (HPC), hypromellose phthalate (HPMCP), hydroxypropyl methylcellulose acetate, hydroxypropyl methylcellulose acetate succinate cellulose (HPMCAS), hydroxyethyl cellulose, carmellose (CMC), carmellose sodium (CMC-Na), carmellose calcium (CMC-Ca), croscarmellose sodium and low-substituted hydroxypropyl cellulose (L-HPC), candela wax, carnauba wax, glycerol monosterate, copovidone, povidone, povidone 12, povidone 25, povidone 30, povidone 90, PEG-4000, PEG-6000, PEG-8000, poloxamer, hydroxy propyl cellulose, hydroxy ethyl cellulose, hydroxy propyl methyl cellulose, hydroxy propyl methyl cellulose acetate succinate, soluplus, corn starch, lactose, maltodextrin, more preferably copovidone, polyvinylpyrrolidone or SOLUPLUS is used. This list is not intended to be comprehensive, as many other excipient substances are useful in the invention.

Removal of solvent in step (b) is accomplished, for example, by substantially complete evaporation of the solvent, concentrating the solution or distillation of solvent, under inert atmosphere to obtain the stable amorphous co-precipitate of Vortioxetine Hydrobromide.

In another embodiment, the solvent is removed by evaporation. Evaporation can be achieved at sub-zero temperatures by lyophilisation or freeze-drying techniques. The solution may also be completely evaporated in, for example, a pilot plant Rota vapor, a Vacuum Paddle Dryer or in a conventional reactor under vacuum above about 720 mm Hg by flash evaporation techniques by using an agitated thin film dryer ("ATFD"), or evaporated by spray drying to obtain a dry amorphous powder.

In another embodiment, the invention provides a process for preparation of a stable co-precipitate of amorphous Vortioxetine hydrobromide comprising the steps of:

a) providing solution of crystalline Vortioxetine adipate in a solvent or mixture thereof;

b) adding a base into the resulting solution of step-a);
c) adding an aqueous solution of hydrobromic acid into resulting solution of step-b);
d) adding suitable pharmaceutical acceptable excipient; into organic layer of resulting solution of step-c);
e) substantially removing solvent from step-d) to a get stable amorphous co-precipitate of Vortioxetine hydrobromide.

According to present invention, base can be selected from, but not limited to, Inorganic bases like sodium hydroxide, potassium hydroxide, ammonium hydroxide, sodium carbonate, ammonia gas, ammonia solution or mixtures thereof, more preferably sodium hydroxide is used.

The amorphous co-precipitate of Vortioxetine hydrobromide with copovidone is having the X-ray powder diffraction (XRD) pattern substantially as depicted in FIG. 4.

In yet another embodiment; the present invention relates to isolated Vortioxetine impurities such as N-oxide impurity and their use as reference standards in a chromatographic method for testing the purity of a Vortioxetine active pharmaceutical ingredient or dosage form.

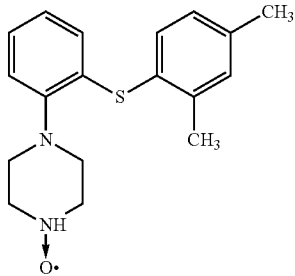

In yet another embodiment; the present invention provides a crystalline form A of Vortioxetine hydrobromide.

In yet another embodiment, crystalline form A of Vortioxetine hydrobromide water content is between 4.2-4.8% w/w.

In yet another embodiment; the present invention provides a crystalline form A of Vortioxetine hydrobromide having an X-ray powder diffractogram comprising at least one peak at diffraction 2-theta angle selected from 11.35±0.2°, 15.30±0.2° and 19.80±0.2°. The crystalline form-A of has an X-ray powder diffraction pattern with characteristics peaks at 11.35±0.2°, 15.30±0.2°, 18.67±0.2° and 19.80±0.2°. A crystalline Vortioxetine hydrobromide form A has XPRD pattern as shown in FIG. 1.

In yet another embodiment; the present invention provides a pharmaceutical composition comprising the crystalline form A of Vortioxetine hydrobromide and at least one pharmaceutically acceptable excipient.

In yet another embodiment, the present invention provides a process for preparation of crystalline form A of Vortioxetine hydrobromide comprising the steps of;
a) providing the solution of Vortioxetine hydrobromide in suitable solvent;
b) isolating crystalline form A of Vortioxetine hydrobromide.

In an illustrative embodiments of the present invention; suitable solvents is selected from water, methanol, ethanol, isopropanol, 2-propanol, 1-butanol, t-butyl alcohol, 1-pentanol, 2-pentanol, amyl alcohol, ethylene glycol, glycerol, acetone, butanone, 2-pentanone, 3-pentanone, methyl butyl ketone, methyl isobutyl ketone, ethyl formate, methyl acetate, ethyl acetate, propyl acetate, t-butyl acetate, isobutyl acetate, toluene, xylene, methylene dichloride, ethylene dichloride, chlorobenzene, acetonitrile, diethyl ether, diisopropyl ether, t-butyl methyl ether, dibutyl ether, tetrahydrofuran, 1,4-dioxane, 2-methoxyethanol, N,N-dimethylformamide, N,N-dimethylacetamide, N-methylpyrrolidone, pyridine, dimethylsulfoxide, sulfolane, formamide, acetamide, propanamide, pyridine, formic acid, acetic acid, propionic acid or mixtures thereof.

In yet another embodiment; the present invention provides a crystalline form Ad of Vortioxetine hydrobromide.

In yet another embodiment, crystalline form Ad of Vortioxetine hydrobromide moisture content is less than 1.0% w/w.

In yet another embodiment; the present invention provides a crystalline form Ad of Vortioxetine hydrobromide having an X-ray powder diffractogram comprising peak at diffraction 2-theta angle selected from 11.25±0.2°, 11.61±0.2°, 12.99±0.2°, 14.40±0.2°, 15.54±0.2°, 16.52±0.2°, 17.09±0.2°, 17.43±0.2°, 18.15±0.2°, 18.66±0.2°, 19.94±0.2°, 20.40±0.2°, 20.90±0.2°, 22.23±0.2°, 22.57±0.2°, 23.2±0.2° and 23.78±0.2°. A crystalline Vortioxetine hydrobromide form Ad has XPRD pattern as shown in FIG. 2.

Crystalline form Ad is anhydrous form and when it exposed to moisture it converts into form A.

In another aspect, the present invention provides a novel crystalline form of Vortioxetine base.

In yet another embodiment; the present invention provides a crystalline Vortioxetine base having an X-ray powder diffractogram comprising peak at diffraction 2-theta angle selected from 4.19±0.2°, 8.39±0.2°, 11.49±0.2°, 14.14±0.2°, 14.57±0.2°, 14.87±0.2°, 15.40±0.2°, 16.63±0.2°, 17.36±0.2°, 19.02±0.2°, 19.55±0.2°, 21.74±0.2°, 23.00±0.2° and 24.35±0.2°. A crystalline Vortioxetine base has XPRD pattern as shown in FIG. 5.

Novel crystalline form of Vortioxetine base can be precipitated from the suitable solvents which are included but not limited up to water, esters, alkanols, halogenated hydrocarbons, ketones, ethers, nitriles, polar aprotic solvents, monoprotic carboxylic acids or mixtures thereof.

The esters may include one or more of methyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of ketones include acetone, methyl ethyl ketone, and the like. Examples of ethers include diethyl ether, tetrahydrofuran, and the like. Examples of nitriles include acetonitrile, benzonitrile. A suitable polar aprotic solvent includes one or more of N,N-dimethylformamide, N,N-dimethylacetamide, dimethylsulphoxide, N-methylpyrrolidone, sulfolane and dimethyl propylene urea. Examples of monoprotic carboxylic acids include formic acid, acetic acid and propionic acid. More preferably sulfolane.

In yet another embodiment; the present invention provides a crystalline form B of Vortioxetine hydrobromide in that the molar ratio of Vortioxetine and the Hydrobromic acid is in the range of from 1:0.5 to 1:1.2, and preferably is approximately 1:0.6.

A crystalline form B of Vortioxetine hydrobromide has an X-ray powder diffractogram comprising peaks at 2-theta angles of 8.42±0.2°, 12.20±0.2°, 14.20±0.2°, and 14.91±0.2°. The crystalline form B of Vortioxetine hydrobromide has XPRD pattern as shown in FIG. 6.

In illustrative embodiments of the present invention; a process for preparation of crystalline form B of Vortioxetine hydrobromide comprising the steps of:

a) passing dry Hydrobromic acid gas in to the solution of Vortioxetine base in the suitable solvent; and
b) isolating the crystalline form-B of Vortioxetine hydrobromide.

Wherein suitable solvent is selected from acetone, N,N-dimethylformamide dimethylsulfoxide, acetonitrile, tetrahydrofuran, methylene dichloride, ethyl acetate, butanone, 2-pentanone, 3-pentanone, methyl butyl ketone, methyl isobutyl ketone, ethyl formate, methyl acetate, propyl acetate, t-butyl acetate, isobutyl acetate, ethylene dichloride, chlorobenzene, diethyl ether, diisopropyl ether, t-butyl methyl ether, dibutyl ether, 1,4-dioxane, 2-methoxyethanol, N,N-dimethylacetamide, N-methylpyrrolidone, sulfolane, formamide, acetamide, propanamide, hexane, cyclohexane, pentane, toluene, xylene or mixtures thereof.

In another embodiment; the present invention encompasses the solvates isolated in pure form or when admixed with other materials, for example other isomers and/or polymorphic forms and/or salt forms or any other material.

Solvates have some variability in the exact molar ratio of their components depending on a variety of conditions understood to a person of skill in the art. For example, a molar ratio of components within a solvate provides a person of skill in the art information as to the general relative quantities of the components of the solvate and in many cases the molar ratio may vary by about plus or minus 20% from a stated range. For example, a molar ratio of 1:1 is understood to include the ratio 1:0.8 as well as 1:1.2 as well as all of the individual ratios in between.

The present invention relates to solvates of Vortioxetine hydrobromide with benzyl alcohol, propylene glycol, dimethyl sulphoxide and diethyl ether.

In specific embodiment the present invention relates to a crystalline benzyl alcohol solvate of Vortioxetine hydrobromide wherein the molar ratio of Vortioxetine hydrobromide to benzyl alcohol is approximately 1:0.5; more specifically, crystalline form C of Vortioxetine hydrobromide benzyl alcohol solvate. The crystalline solvates of the present invention may have advantages relative to other known forms of Vortioxetine hydrobromide, including chemical stability, polymorphic stability and/or varying solubility.

The crystalline form C of Vortioxetine hydrobromide benzyl alcohol solvate of present invention can be characterized by showing an X-ray powder diffractogram comprising characteristic peaks (expressed in 2θ±0.2°θ, CuKα radiation) at 8.28±0.2° 8.85±0.2°, 11.84±0.2°, 14.22±0.2°, 14.75±0.2°, 15.00±0.2°, 16.13±0.2°, 16.59±0.2°, 17.65±0.2°, 18.18±0.2°, 19.02±0.2° and 19.24±0.2°. A representative diffractogram is displayed in FIG. 8.

In illustrative embodiments of present invention, there is provided a Form C of Vortioxetine hydrobromide benzyl alcohol solvate described herein characterized by a Diffraction Scanning Calorimetry as depicted in FIG. 11.

The DSC thermogram for form C of Vortioxetine hydrobromide benzyl alcohol, shown in FIG. 11, indicates an endotherm onset at 140-150° C., at scan rate of 10° C./min.

In illustrative embodiments of the present invention, there is provided a process for preparation of Vortioxetine hydrobromide benzyl alcohol solvate, the process comprising:

a. contacting Vortioxetine free base with benzyl alcohol in solution or suspension;
b. treating the resulting solution or suspension of step-a with Hydrobromic acid;
c. crystallizing the benzyl alcohol solvate of Vortioxetine hydrobromide;
d. isolating the solvate.

In illustrative embodiments of the present invention; Vortioxetine free base solution or suspension can be prepared by dissolving it in solvent like water, esters, alkanols, aliphatic and cyclic hydrocarbons, halogenated hydrocarbons, ketones, ethers, nitriles, polar aprotic solvents, carboxylic acid or mixtures thereof. The esters may include one or more of ethyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of aliphatic hydrocarbons include hexane, heptane, and octane. Examples of cyclic hydrocarbons include cylohexane, cycloheptane and cyclooctane. Examples of halogenated hydrocarbons include dichloromethane, chloroform, and 1,2-dichloroethane. Examples of ketones include acetone, methyl ethyl ketone, and the like. Examples of ethers include diethyl ether, tetrahydrofuran, and the like. Examples of nitriles include acetonitrile, benzonitrile. A suitable polar aprotic solvent includes one or more of N,N-dimethylformamide, N,N-dimethylacetamide, dimethylsulphoxide, acetonitrile and N-methylpyrrolidone, Examples of carboxylic acid include acetic acid, propionic acid, fumaric acid.

In illustrative embodiments of the present invention, hydrobromic acid may be provided as a gas or as a solution in an organic or aqueous solvent.

In illustrative embodiments of the present invention, crystallizing the benzyl alcohol solvate may be induced by cooling and/or seeding. Following crystallization, a suspension may be formed and the suspension may be maintained at a temperature of about 20° C. to about 40° C. prior to isolation of the crystals.

In illustrative embodiments of the present invention, Vortioxetine hydrobromide benzyl alcohol solvate can be crystallized by use of solvent like water, esters, alkanols, aliphatic and cyclic hydrocarbons, halogenated hydrocarbons, ketones, ethers, polar aprotic solvents, carboxylic acids or mixtures thereof. The esters may include one or more of ethyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of aliphatic hydrocarbons include hexane, heptane, and octane. Examples of cyclic hydrocarbons include cylohexane, cycloheptane and cyclooctane. Examples of halogenated hydrocarbons include dichloromethane, chloroform, and 1,2-dichloroethane. Examples of ketones include acetone, methyl ethyl ketone, and the like. Examples of ethers include diethyl ether, tetrahydrofuran, and the like. A suitable polar aprotic solvent includes one or more of N,N-dimethylformamide, N,N-dimethylacetamide, dimethylsulphoxide, acetonitrile and N-methylpyrrolidone. Examples of carboxylic acids include acetic acid, propionic acid, fumaric acid. More preferably hydrocarbons like hexane, heptanes, cyclohexane is used.

In illustrative embodiments of the present invention, the Vortioxetine hydrobromide benzyl alcohol solvate can be isolated by using technique like filtration or distillation.

In illustrative embodiments of the present invention, there is provided a process for preparation of Vortioxetine hydrobromide benzyl alcohol solvate, the process comprising:

a. contacting Vortioxetine hydrobromide with benzyl alcohol;
b. crystallizing the benzyl alcohol solvate of Vortioxetine hydrobromide;
c. isolating the solvate.

In illustrative embodiments of the present invention, there is provided a process for preparation of Vortioxetine hydrobromide benzyl alcohol solvate, the process comprising:
a. contacting Vortioxetine acid addition salt with base in solution;
b. treating the resulting solution of step-a with hydrobromic acid;
c. treating the resulting solution of step-b with benzyl alcohol in solution;
d. crystallizing the benzyl alcohol solvate of Vortioxetine hydrobromide;
e. isolating the solvate.

In illustrative embodiments of the present invention, Vortioxetine acid addition salt includes but not limited to Vortioxetine adipate, Vortioxetine pyruvate, Vortioxetine malonate and Vortioxetine glutarate.

In illustrative embodiments of the present invention, base can be selected from inorganic base or organic base. Examples of inorganic base includes but not limited to KOH, NaOH, $K_2CO_3$, $Na_2CO_3$, $NH_3$. Examples of organic base includes but not limited to triethyl amine, methyl amine, pyridine, histidine. More preferably sodium hydroxide is used.

In illustrative embodiments of the present invention, Vortioxetine acid addition solution can be prepared by dissolving Vortioxetine acid addition salt in solvent like water, esters, alkanols, aliphatic and cyclic hydrocarbons, halogenated hydrocarbons, ketones, ethers, polar aprotic solvents, or mixtures thereof. The esters may include one or more of ethyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of aliphatic hydrocarbons include hexane, heptane, and octane. Examples of cyclic hydrocarbons include cylohexane, cycloheptane and cyclooctane. Examples of halogenated hydrocarbons include dichloromethane, chloroform, and 1,2-dichloroethane. Examples of ketones include acetone, methyl ethyl ketone, and the like. Examples of ethers include diethyl ether, tetrahydrofuran, and the like. A suitable polar aprotic solvent includes one or more of N,N-dimethylformamide, N,N-dimethylacetamide, dimethylsulphoxide, acetonitrile and N-methylpyrrolidone. More preferably water is used.

In illustrative embodiments of the present invention, the Hydrobromic acid may be provided as a gas or as a solution in an organic or aqueous solvent.

In illustrative embodiments of the present invention, crystallizing the benzyl alcohol solvate may be induced by cooling and/or seeding. Following crystallization, a suspension may be formed and the suspension may be maintained at a temperature of about 20° C. to about 40° C. prior to isolation of the crystals.

In illustrative embodiments of the present invention, Vortioxetine hydrobromide benzyl alcohol solvate can be crystallized by use of solvent like water, esters, alkanols, aliphatic and cyclic hydrocarbons, halogenated hydrocarbons, ketones, ethers, polar aprotic solvents, or mixtures thereof. The esters may include one or more of ethyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of aliphatic hydrocarbons include hexane, heptane, and octane. Examples of cyclic hydrocarbons include cylohexane, cycloheptane and cyclooctane. Examples of halogenated hydrocarbons include dichloromethane, chloroform, and 1,2-dichloroethane. Examples of ketones include acetone, methyl ethyl ketone, and the like. Examples of ethers include diethyl ether, tetrahydrofuran, and the like. A suitable polar aprotic solvent includes one or more of N,N-dimethylformamide, N,N-dimethylacetamide, dimethylsulphoxide, acetonitrile and N-methylpyrrolidone. More preferably hydrocarbons like hexane, heptanes, cyclohexane is used.

Yet another embodiment of the present invention provides a novel solvate Vortioxetine hydrobromide diethyl ether solvate. A process for preparation of Vortioxetine diethyl ether solvate comprising; the step of achieving a solution of Vortioxetine hydrobromide in diethyl ether. A crystalline form of Vortioxetine hydrobromide diethyl ether solvate of present invention can be characterized by showing an X-ray powder diffractogram comprising characteristic peaks at 2-theta angles of 8.34±0.2°, 12.98±0.2°, 15.30±0.2°, 16.67±0.2° and 17.20±0.2°. A crystalline Vortioxetine hydrobromide diethyl ether solvate has XPRD pattern as shown in as shown in FIG. 16.

In yet another embodiment of the invention is to provide an improved process for the preparation of beta (β) crystalline form of Vortioxetine hydrobromide comprising,
a. providing solution of Vortioxetine base using organic solvent or mixture thereof;
b. adding Hydrobromic acid solution into resulting solution of step-a;
c. collecting crystalline beta form of Vortioxetine hydrobromide.

Solution can be provided by dissolving Vortioxetine base in solvents selected from water, esters, alkanols, halogenated hydrocarbons, ketones, ethers, nitriles, polar aprotic solvents, monoprotic carboxylic acids or mixtures thereof. The esters may include one or more of methyl acetate, n-propyl acetate, isopropyl acetate, and n-butyl acetate. Examples of alkanols include those primary, secondary and tertiary alcohols having from one to six carbon atoms. Suitable alkanol solvents include methanol, ethanol, n-propanol, isopropanol and butanol. Examples of ketones include acetone, methyl ethyl ketone, and the like. Examples of ethers include diethyl ether, tetrahydrofuran, and the like. Examples of nitriles include acetonitrile, benzonitrile. A suitable polar aprotic solvent includes one or more of N,N-dimethylformamide, N,N-dimethylacetamide, dimethylsulphoxide, N-methylpyrrolidone, sulfolane and dimethyl propylene urea. Examples of monoprotic carboxylic acids include formic acid, acetic acid and propionic acid. More preferably solvents such as water, MIBK, acetic acid, DMSO, toluene, THF, acetonitrile, methyl acetate, ethanol, methanol and aqueous ethanol or mixtures thereof is used.

Hydrobromic acid solution may be aqueous or in acetic acid.

In another embodiment the Vortioxetine Hydrobromide disclosed herein for use in the pharmaceutical compositions of the present invention, wherein 90 volume-percent of the particles (D90) have a size of less than or equal to about 500 microns, specifically less than or equal to about 300 microns, more specifically less than or equal to about 200 microns, still more specifically less than or equal to about 100 microns, and most specifically less than or equal to about 15 microns.

EXAMPLES

The following examples are provided to enable one skilled in the art to practice the invention and are merely illustrate the process of this invention. However, it is not intended in any way to limit the scope of the present invention.

1H NMR spectra are recorded at 300 MHz on a Bruker Avance III instrument. Dimethyl sulfoxide (99.8% D) is used as solvent, and tetramethylsilane (TMS) is used as internal reference standard.

The melting points are measured using Differential Scanning Calorimetry (DSC). The equipment is a TA-Instruments DSC-Q1000 calibrated at 10°/min to give the melting point as onset value. About 2 mg of sample is heated 10°/min in a loosely closed pan under nitrogen flow.

Thermo gravimetric analysis (TGA) used for estimation of solvent/water content of dried material is performed using a TA-instruments TGA-Q500 about 10 mg sample is heated 10°/min in an open pan under nitrogen flow.

X-Ray powder diffractograms were measured on a PANalytical X'Pert PRO X-Ray Diffractometer using CuKα1 radiation. The samples were measured in reflection mode in the 2θ-range 2.5-40° using an X'celerator detector.

The FTIR spectrum was collected at 4 cm resolution using a Perkin Elmer Paragon 1100 single beam FTIR instrument. The samples were intimately mixed in an approximately 1:100 ratio (w/w) with potassium bromide using an agate mortar and pestle to a fine consistency; the mixture was compressed in a pellet die at a pressure of 5 to 10 tonnes for a time period between 2 and 5 minutes. The resulting disk was scanned 5 times versus a collected background. Data was baseline corrected and normalized.

Example-1

Preparation of 2,4-dimethyl-1-[(2-nitrophenyl)sulfanyl]benzene 2,4-dimethylbenzenethiol (5.0 g), 1-fluoro-2-nitrobenzene (5.2 g), potassium carbonate (10.0 g) and Dimethyl formamide (50 ml) were introduced into round bottom flask at temperature 30±5° C. The reaction mixture was heated at 85±5° C. for two hr. After completion reaction mixture was cooled to 25±5° C. Process water (250 ml) was added into reaction mixture at 0-5° C. Reaction mixture was stirred for 30 min at 0-10° C. Reaction mixture was filtered and process water (250 ml) was added at 20-25° C. Reaction mixture was heated to 45±5° C. for 15 min. Solid material was isolated by filtration and dried it at 60° C.

Example-2

Preparation of 2-[(2,4-dimethylphenyl)sulfanyl]aniline 2,4-dimethyl-1-[(2-nitrophenyl)sulfanyl]benzene (52.5 g)), iron powder (52.5 g), ammonium chloride (10.5 g) and water (1050 ml) was added into round bottom flask at 30±5° C. The reaction mixture was heated to 85±5° C. for about 3-4 hrs. After completion of reaction, the reaction mixture was cooled to room temperature, filtered to remove metal catalyst and the compound was extracted with toluene (2×1050 ml). Toluene was distilled out under vacuum to give the desired compound. Residual mass was dissolved in dichloromethane and into this resulting solution, Methanolic HCl (128 ml, Assay=7.7%, 1.25 eq) was added at 30±5° C. The reaction mixture was stirred for 40° C. for 15-30 minutes then, Dichloromethane and methanol was distilled out under vacuum at 55° C. Cyclohexane was added into resulting solid mass and stirred it for 1 hr at 30±5° C. Resulting mixture was filtered and then solid mass was dissolved in acetone at reflux temperature for 1 hr then reaction mixture was cooled to 30±5° C. Resulting reaction mixture was filtered and it was dissolved in dichloromethane, into this solution 10% NaOH solution was added (pH >10). Organic layer was separated out and was distilled out to collect 2-[(2,4-dimethylphenyl)sulfanyl]aniline.

Example-3

Preparation of Vortioxetine Adipate

2-[(2,4-dimethylphenyl)sulfanyl]aniline (20 g), o-Xylene (60 ml), Bis(2-chloroethyl)amine hydrochloride (15.59 g) and PTSA (0.5 g) was added into round bottom flask. The reaction mixture was heated at 140±7° C. Reaction mixture was stirred for 30 hr at reflux temperature. Reaction mixture was cooled to 30±5° C. and then, o-Xylene (200 ml) and water (160 ml) was added to the reaction mixture at 30±5° C. Resulting reaction mixture was basified with 10% NaOH (pH >7.0) at 30±5° C. Organic layer was separated out and into resulting organic layer, adipic acid solution (12.8 g) in Acetone (306 ml) was added at 40° C. Resulting reaction mixture was stirred for 2 hr at 30±5° C. Reaction mixture was filtered and solid mass was washed with acetone (20 ml) and dried it under vacuum for 6-8 hrs at 55±5° C. Resulting crude Vortioxetine adipate salt was added in THF (500 ml) at 30±5° C. Resulting reaction mixture was heated to reflux temperature for 5-10 mins. Resulting reaction mixture was cooled to 30±5° C. and stirred it for 1 hr at 30±5° C. and pure Vortioxetine adipate salt was collected by filtration.

Example-4

Preparation of 1-[2-(2,4-Dimethyl-phenylsulfanyl)-phenyl]-piperazine malonate

Vortioxetine adipate (5 gm) and water (25 ml) were added into round bottom flask at 30±5° C. Into this reaction mixture, ethyl acetate (10 ml) was added at 30±5° C. Resulting reaction mixture was basified using 10% NaOH solution (pH>7.0) (7.5 ml) at 30±5° C. and was stirred it for 10 min. Organic layer was separated and it was heated up to reflux temperature. Malonic acid solution (malonic acid solution is prepared by dissolving 1.13 g malonic acid into Ethyl acetate (14 ml) at reflux temperature) was added into this organic layer and reaction mixture was stirred for 15-30 mins at reflux temperature. Reaction mixture was cooled to 30±5° C. Reaction mixture was filtered to get solid mass and was dried under vacuum for 6-8 hrs at 55±5° C.

Example-5

Preparation of 1-[2-(2,4-Dimethyl-phenylsulfanyl)-phenyl]-piperazine pyruvate

Vortioxetine adipate (5 gm) and water (25 ml) were added into round bottom flask at 30±5° C. Into this reaction mixture, ethyl acetate (10 ml) was added at 30±5° C.

Resulting reaction mixture was basified using 10% NaOH solution (pH>7.0) (7.5 ml) at 30±5° C. and was stirred it for 10 min. Organic layer was separated and it was heated up to reflux temperature. Pyruvic acid solution (pyruvic acid solution is prepared by dissolving 0.96 g pyruvic acid into Ethyl acetate (5.5 ml) at reflux temperature) was added into this organic layer and reaction mixture was stirred for 15-30 mins at reflux temperature. Reaction mixture was cooled to 30±5° C. Reaction mixture was filtered to get solid mass and was dried under vacuum for 6-8 hr at 55±5° C.

Example-6

Preparation of 1-[2-(2,4-Dimethyl-phenylsulfanyl)-phenyl]-piperazine glutarate

Vortioxetine adipate (5 gm) and water (25 ml) were added into round bottom flask at 30±5° C. Into this reaction mixture, ethyl acetate (10 ml) was added at 30±5° C. Resulting reaction mixture was basified using 10% NaOH solution (pH>7.0) (7.5 ml) at 30±5° C. and was stirred it for 10 min. Organic layer was separated and it was heated up to reflux temperature. Glutaric acid solution (glutaric acid solution is prepared by dissolving 1.29 g glutaric acid into Ethyl acetate (60 ml) at reflux temperature) was added into this organic layer and reaction mixture was stirred for 15-30 mins at reflux temperature. Reaction mixture was cooled to 30±5° C. Reaction mixture was filtered to get solid mass and was dried under vacuum for 6-8 hrs at 55±5° C.

Example-7

Preparation of 1-[2-(2,4-Dimethyl-phenylsulfanyl)-phenyl]-piperazine hydrobromide form B Vortioxetine adipate (30.0 g) and dichloromethane (450 ml) were charged in round bottom flask. The reaction mixture was stirred for 5 min then it was basified with NaOH solution (8.1 g in 300 ml water). Solution of NaCl (7.5 g in 75 ml water) was added into above reaction mixture. Organic layer was separated out and distilled out from reaction mixture to remove water azeotropically to get clear solution. Dichloromethane (300 ml) was added into above clear solution and stirred it for 10 min. Dry HBr was purged into the resulting reaction mixture for 1 hr. After completion of reaction dichloromethane was distilled out and dried under vacuum for 6 hr at 40° C. to get Vortioxetine hydrobromide Form B.

Example-8

Preparation of 1-[2-(2,4-Dimethyl-phenylsulfanyl)-phenyl]-piperazine hydrobromide diethylether solvate Vortioxetine adipate (30.0 g) and dichloromethane (450 ml) were charged in round bottom flask. The reaction mixture was stirred for 5 min then it was basified with NaOH solution (8.1 g in 300 ml water). Solution of NaCl (7.5 g in 75 ml water) was added into above reaction mixture. Organic layer was separated out and into this organic layer, aqueous HBr (12.0 g) was added and stirred it for 30 min. Organic layer was separated out and distilled out from reaction mixture to remove water azeotropically to get clear solution. Dichloromethane (300 ml) was added into above clear solution. Reaction mixture was stirred for 10 min. Resulting reaction mixture was added into cooled diethyl ether (1500 ml) solvent at −65 to −70° C. and was stirred it for 30 min. Reaction mixture was distilled out to get solid mass and dried it at 40° C. under vacuum for 6 hour to get Vortioxetine hydrobromide diethyl ether solvate.

Example-9

Preparation of Amorphous Form of Vortioxetine Hydrobromide

Vortioxetine adipate (30.0 g) and dichloromethane (450 ml) were charged in round bottom flask. The reaction mixture was stirred for 5 min then it was basified with NaOH solution (8.1 g in 300 ml water). Solution of NaCl (7.5 g in 75 ml water) was added into above reaction mixture. Organic layer was separated out. Aqueous HBr (11.48 g) was added into the organic layer and stirred it for 30 min. Organic layer was separated out and distilled out dichloromethane to remove water azeotropically; Dichloromethane (300 ml) was added into above clear solution and was stirred it for 10 min. The reaction mixture was filtered through hyflo at 30±5° C. and spray dried to get amorphous Vortioxetine hydrobromide. Solid was dried at 40° C. for 6 hours.
Condition of Spray Drying
Feeding rate of solution: 6 rpm to 10 rpm.
Nitrogen/Air pressure: 3 kg to 5 kg
Temperature of spray gun inlet: 55 to 60° C.
Vacuum of spray dryer: 50-90 mmHg
Humidity of working area: less than 40% RH Example-10

Preparation of an Amorphous Co-precipitate of Vortioxetine Hydrobromide with Copovidone Vortioxetine adipate (30.0 g) and dichloromethane (450 ml) were charged in round bottom flask. The reaction mixture was stirred for 5 min then it was basified with NaOH solution (8.1 g in 300 ml water). Solution of NaCl (7.5 g in 75 ml water) was added into above reaction mixture. Organic layer was separated out. Aqueous HBr (11.48 g) was added into organic layer and stirred it for 30 min. After completion of reaction dichlormethane was distilled out to remove water azeotropically; Dichloromethane (300 ml) and copovidone (12.8 g) were added into it and stirred it for 10 min. The reaction mixture was filtered through hyflo at 30±5° C. and spray dried to get an amorphous co-precipitate Vortioxetine hydrobromide with copovidone. The resulting solid was dried at 60° C. under vacuum for 6 hours.
Condition of Spray Drying
Feeding rate of solution: 6 rpm to 10 rpm.
Nitrogen/Air pressure: 3 kg to 5 kg
Temperature of spray gun inlet: 55 to 60° C.
Vacuum of spray dryer: 50-90 mmHg
Humidity of working area: less than 40% RH Example 11

Preparation of an Amorphous Co-precipitate of Vortioxetine Hydrobromide with PVP K-90

Vortioxetine adipate (30.0 g) and dichloromethane (450 ml) were charged in round bottom flask. The reaction mixture was stirred for 5 min then it was basified with NaOH solution (8.1 g in 300 ml water). Solution of NaCl (7.5 g in 75 ml water) was added into above reaction mixture.

Organic layer was separated out and was distilled out to remove water azeotropically; Dichloromethane (250) and HBr in acetic acid (16.83 g) were added into resulting clear solution and stirred it for 10 min. PVP K-90 (12.8 g) was added into it and stirred it for 10 min. The reaction mixture was filtered through hyflo at 30±5° C. and spray dried to get an amorphous co-precipitate of Vortioxetine hydrobromide with PVP K-90. The resulting solid was dried at 60° C. under vacuum for 6 hours.

Condition of Spray Drying
Feeding rate of solution: 6 rpm to 10 rpm.
Nitrogen/Air pressure: 3 kg to 5 kg
Temperature of spray gun inlet: 55 to 60° C.
Vacuum of spray dryer: 50-90 mmHg
Humidity of working area: less than 40% RH Example 12

Preparation of an Amorphous Co-precipitate of Vortioxetine Hydrobromide with SOLUPLUS Vortioxetine adipate (30.0 g) and dichloromethane (450 ml) were charged in round bottom flask. The reaction mixture was stirred for 5 min then it was basified with NaOH solution (8.1 g in 300 ml water). Solution of NaCl (7.5 g in 75 ml water) was added into above reaction mixture. Organic layer was separated out and was distilled out to remove water azeotropically; Dichloromethane (250) and HBr in acetic acid (16.83 g) were added into resulting clear solution and stirred it for 10 min. SOLUPLUS (12.8 g) was added into it and stirred it for 10 min. The reaction mixture was filtered through hyflo at 30±5° C. and spray dried to get an amorphous co-precipitate of vortioxetine hydrobromide with SOLUPLUS. The resulting solid was dried at 60° C. under vacuum for 6 hours.

Condition of Spray Drying:
Feeding rate of solution: 6 rpm to 10 rpm.
Nitrogen/Air pressure: 3 kg to 5 kg
Temperature of spray gun inlet: 55 to 60° C.
Vacuum of spray dryer: 50-90 mmHg
Humidity of working area: less than 40% RH Example-13a Preparation of Vortioxetine Hydrobromide Benzyl Alcohol Solvate Vortioxetine Adipate (30.0 g) and dichloromethane (300 ml) were added into round bottom flask and stirred it for 5 mins. Solution of NaOH (8.1 g in 300 ml water) and solution of NaCl (7.5 g in 75 ml water) were added into above resulting solution and stirred it till clear solution was observed. Organic layer was separated out and washed it with water for two times. Organic layer was filtered through hyflo bed and benzyl alcohol (40 ml) was charged into organic layer. Dichloromethane was distilled out and degassed it at 70° C. for 1 hour. Reaction mass was cooled to 15-20° C. Aqueous HBr (10.75 g) was added into resulting reaction mass and stirred it for 30 mins. Cyclohexane (50 ml) was added to solid residue and stirred it for 10 mins. Cyclohexane was distilled out from reaction mixture and degassed residue at 30-40° C. for 3 hours. Cyclohexane (150 ml) again was added into solid residue and stirred it for 30 mins. Reaction mixture was filtered and dried at 60° C. under vacuum for 8 hours to get Vortioxetine hydrobromide benzyl alcohol solvate.

Example-13b

Preparation of Vortioxetine Hydrobromide Benzyl Alcohol Solvate

Vortioxetine Adipate (30.0 g) and dichloromethane (300 ml) were added into round bottom flask and stirred it for 5 mins. Solution of NaOH (8.1 g in 300 ml water) and solution of NaCl (7.5 g in 75 ml water) were added into above resulting solution and stirred it till clear solution was observed. Organic layer was separated out and washed it with water for two times. Organic layer was filtered through hyflo bed and benzyl alcohol (40 ml) was charged into organic layer. Dichloromethane was distilled out and degassed it at 70° C. for 1 hour. Reaction mass was cooled to 15-20° C. HBr in acetic acid (15.2 g) was charged into reaction mass and stirred it for 30 mins. Cyclohexane (50 ml) was added to solid residue and stirred it for 10 mins. Cyclohexane was distilled out from reaction mixture and degassed residue at 30-40° C. for 3 hours. Cyclohexane (150 ml) again was added into solid residue and stirred it for 30 mins. Reaction mixture was filtered and dried at 60° C. under vacuum for 8 hours to get vortioxetine hydrobromide benzyl alcohol solvate.

Example-13c

Preparation of Vortioxetine Hydrobromide Benzyl Alcohol Solvate

Vortioxetine Adipate (30.0 g) and cyclohexane (450 ml) were added into round bottom flask and stirred it for 5 mins. Solution of NaOH (8.1 g in 300 ml water) and solution of NaCl (7.5 g in 75 ml water) were added into above resulting solution and stirred it till clear solution was observed. Organic layer was separated out and washed it with water for two times. Organic layer was filtered through hyflo bed and benzyl alcohol (40 ml) was charged into organic layer. Dichloromethane was distilled out and degassed it at 70° C. for 1 hour. Reaction mass was cooled to 15-20° C. Aqueous HBr (10.75 g) was added into resulting reaction mass and stirred it for 30 mins. Cyclohexane (50 ml) was added to solid residue and stirred it for 10 mins. Cyclohexane was distilled out from reaction mixture and degassed residue at 30-40° C. for 3 hours. Cyclohexane (150 ml) again was added into solid residue and stirred it for 30 mins. Reaction mixture was filtered and dried at 60° C. under vacuum for 8 hours to get Vortioxetine hydrobromide benzyl alcohol solvate.

Example-13d

Preparation of Vortioxetine Hydrobromide Benzyl Alcohol Solvate

Prepared a solution of 10 g of Vortioxetine hydrobromide in 10 ml of benzyl alcohol and allowed to crystallise at room temperature. Stirred the slurry with 20 ml hexane and then filtered the solid.

Example-14

Process for the Preparation of Vortioxetine Hydrobromide (Form Ad)

Vortioxetine Adipate (30.0 g) and dichloromethane (450 ml) were charged in round bottom flask stirred it for 5 mins.

Solution of NaOH (8.1 g in 300 ml water) and solution of NaCl (7.5 g in 75 ml water) were added into above resulting solution and stirred it till clear solution was observed. Organic layer was separated out. HBr in acetic acid (18 g) was added into organic layer and stirred it for 30 mins. Acetic acid (150 ml) was added into reaction mixture. Dichloromethane was distilled out atmospherically from reaction mixture. Acetic acid (200 ml) and water (50 ml) were added into the reaction mixture. Water (1250 ml) was taken into another round bottom flask at 30±5° C. and cooled to 7±3° C. Reaction mixture was added into water containing round bottom flask within 15-30 minutes at 7±3° C. and after addition, reaction mixture's temperature allowed to come to 20±2° C. Reaction mixture was stirred for 30 minutes at 20±2° C. Reaction mixture was filtered and washed it with water (50 ml). Solid was dried to get Vortioxetine Hydrobromide (Form Ad) under vacuum for 6-8 hrs at 45±3° C. (Moisture content of solid is less than 1.0% w/w)

Example-15

Process for the Preparation of Vortioxetine Hydrobromide (Form A)

Vortioxetine Adipate (30.0 g) and dichloromethane (450 ml) were charged in round bottom flask stirred it for 5 mins. Solution of NaOH (8.1 g in 300 ml water) and solution of NaCl (7.5 g in 75 ml water) were added into above resulting solution and stirred it till clear solution was observed. Organic layer was separated out. HBr in acetic acid (18 g) was added into organic layer and stirred it for 30 mins. Acetic acid (150 ml) was added into reaction mixture. Dichloromethane was distilled out atmospherically from reaction mixture. Acetic acid (200 ml) and water (50 ml) were added into the reaction mixture. Water (1250 ml) was taken into another round bottom flask at 30±5° C. and cooled to 7±3° C. Reaction mixture was added into water containing round bottom flask within 15-30 minutes at 7±3° C. and after addition, reaction mixture's temperature allowed to come to 20±2° C. Reaction mixture was stirred for 30 minutes at 20±2° C. Reaction mixture was filtered and washed it with water (50 ml). Solid was dried to get Vortioxetine Hydrobromide (Form Ad) under vacuum for 6-8 hrs at 45±3° C. (Moisture content of Vortioxetine Hydrobromide (Form Ad) is less than 1.0% w/w). Vortioxetine Hydrobromide (Form Ad) was exposed at 40% RH and 25° C. for 2 hours to get Vortioxetine Hydrobromide (Form A). (Moisture content of Vortioxetine Hydrobromide (Form A) is between 4.2-4.8% w/w)

Example-16a

Process of Vortioxetine Hydrobromide Beta Form

Vortioxetine Adipate (30.0 g) and dichloromethane (450 ml) were charged in round bottom flask and stirred it for 5 mins. Solution of NaOH (8.1 g in 300 ml water) and solution of NaCl (7.5 g in 75 ml water) were added into above resulting solution and stirred it till clear solution was observed. Organic layer was separated out. Water (300 ml) was charged into organic layer and stirred it for 10 mins. Organic layer was separated out and distilled out dichloromethane atmospherically at 50° C. Acetic acid (105 ml) was added to the reaction mixture at 50° C. and stirred it at 45-50° C. until clear solution observed. Traces of dichloromethane were removed under vacuum at 50° C. Reaction mixture was cooled to 25-30° C. Aqueous HBr solution (11.95 g, assay-48%) was added to reaction mixture at 25-30° C. and stirred it at 25-30° C. Reaction mixture was filtered and washed it with Acetic acid (15 ml) at 25-30° C. Solid was dried to get vortioxetine hydrobromide (Beta form) under vacuum for 8-10 hrs at 50-60° C.

Example-16b

Process of Vortioxetine Hydrobromide Beta Form

Vortioxetine Adipate (30.0 g) and Toluene (450 ml) were charged in round bottom flask and stirred it for 5 mins. Solution of NaOH (8.1 g in 300 ml water) and solution of NaCl (7.5 g in 75 ml water) were added into above resulting solution and stirred it till clear solution was observed. Organic layer was separated out. Water (300 ml) was charged into organic layer and stirred it for 10 mins. Organic layer was separated out and heated to 75-85° C. Aqueous HBr solution (11.95 g, assay-48%) was added to reaction mixture at 75-85° C. and stirred it for 30 mins at 75-85° C. Reaction mixture was cooled to 25-30° C. and stirred it for 30 mins. Reaction mixture was filtered and washed it with toluene (15 ml) at 25-30° C. Solid was dried to get vortioxetine hydrobromide (Beta form) under vacuum for 8-10 hrs at 50-60° C.

Example-17

Preparation of Vortioxetine Base (Novel Polymorph)

Vortioxetine Adipate (30.0 g) and dichloromethane (450 ml) were charged in round bottom flask and stirred it for 5 mins. Solution of NaOH (8.1 g in 300 ml water) and solution of NaCl (7.5 g in 75 ml water) were added into above resulting solution and stirred it till clear solution was observed. Organic layer was separated out. Water (300 ml) was charged into organic layer and stirred it for 10 mins. Organic layer was separated out. Sulfolane (200 ml) was added to organic layer and stirred it for 30 min. Dichloromethane was distilled out from reaction mixture. Resulting reaction mixture was filtered and washed with water (50 ml) to get crystalline vortioxetine base.

The invention claimed is:
1. A crystalline form C of Vortioxetine hydrobromide benzyl alcohol solvate having an X-ray powder diffractogram ("XPRD") comprising peaks at 2-theta angles of 8.26±0.2°, 8.85±0.2°, 17.63±0.2° and 19.01±0.2°.
2. The crystalline form C of Vortioxetine hydrobromide benzyl alcohol solvate according to claim 1 having a molar ratio of Vortioxetine hydrobromide to benzyl alcohol of approximately 1:0.5.
3. The crystalline form C of Vortioxetine hydrobromide benzyl alcohol solvate according to claim 1 having an XPRD pattern as shown in FIG. 8.
4. A process for preparation of crystalline form C of Vortioxetine hydrobromide benzyl alcohol solvate according to claim 1 comprising:
   a) providing a solution of Vortioxetine hydrobromide in benzyl alcohol solvent; and
   b) isolating a crystalline form C of Vortioxetine hydrobromide benzyl alcohol solvate from the solution.
5. The crystalline form C of Vortioxetine hydrobromide benzyl alcohol solvate of claim 1, wherein having an X-ray powder diffractogram comprising peaks at 2-theta angles of 11.84±0.2°, 14.75±0.2° 16.11±0.2°, and 23.12±0.2°.

\* \* \* \* \*